(12) United States Patent
Richter et al.

(10) Patent No.: US 11,707,565 B2
(45) Date of Patent: Jul. 25, 2023

(54) MEDICAL PUMP

(71) Applicant: SANOFI, Paris (FR)

(72) Inventors: René Richter, Tharandt (DE); Sebastian Pech, Dresden (DE); Jens Lienig, Berlin (DE)

(73) Assignee: Sanofi, Paris (FR)

( * ) Notice: Subject to any disclaimer, the term of this patent is extended or adjusted under 35 U.S.C. 154(b) by 169 days.

(21) Appl. No.: 16/755,367

(22) PCT Filed: Oct. 19, 2018

(86) PCT No.: PCT/EP2018/078684
§ 371 (c)(1),
(2) Date: Apr. 10, 2020

(87) PCT Pub. No.: WO2019/077097
PCT Pub. Date: Apr. 25, 2019

(65) Prior Publication Data
US 2021/0252214 A1    Aug. 19, 2021

(30) Foreign Application Priority Data
Oct. 19, 2017  (EP) ................................. 17306415

(51) Int. Cl.
*A61M 5/142*    (2006.01)
(52) U.S. Cl.
CPC . *A61M 5/14216* (2013.01); *A61M 2205/3327* (2013.01)
(58) Field of Classification Search
CPC ............ A61M 5/14216; A61M 5/1422; A61M 5/14212; A61M 5/16809; F04B 7/04;
(Continued)

(56) References Cited

U.S. PATENT DOCUMENTS

| | | | |
|---|---|---|---|
| 2007/0221275 A1* | 9/2007 | Amley | A61M 39/223 137/512 |
| 2008/0139996 A1* | 6/2008 | Bowman | A61M 5/16859 604/67 |
| 2008/0294040 A1* | 11/2008 | Mohiuddin | F04B 13/00 600/432 |
| 2010/0286602 A1* | 11/2010 | Carter | A61M 5/14244 604/67 |

(Continued)

FOREIGN PATENT DOCUMENTS

| CN | 104797279 | 7/2015 |
|---|---|---|
| CN | 205658923 | 10/2016 |

(Continued)

OTHER PUBLICATIONS

Neidl (DE612248C)—Machine translated specification (Year: 1935).*

(Continued)

*Primary Examiner* — James D Ponton
(74) *Attorney, Agent, or Firm* — Fish & Richardsosn P.C.

(57) ABSTRACT

The present disclosure relates to a medical pump for dispensing a liquid. The medical pump includes a housing, a receptacle and a piston. The housing includes an inlet for receiving said liquid and an outlet for dispensing said liquid. The receptacle includes a chamber and a passage that is in fluid communication with the chamber. The receptacle is received in the housing and is axially movable relative to the housing from a filling position, wherein the passage fluidly communicates the chamber with the inlet, to a dispensing position, wherein the passage fluidly communicates the chamber with the outlet. The piston is received in the chamber and is configured such that when the receptacle is in the filling position the piston is axially moveable relative to the receptacle and when the receptacle is in the dispensing position the piston is axially moveable relative to the receptacle.

17 Claims, 10 Drawing Sheets

(58) Field of Classification Search
CPC .......... F04B 3/00; F04B 7/0015; F04B 3/003; F04B 7/0291; F04B 7/0053
See application file for complete search history.

(56) References Cited

U.S. PATENT DOCUMENTS

2010/0303656 A1   12/2010   Lin et al.
2013/0053816 A1*   2/2013   Diperna .............. A61M 5/1408
                                                              604/500

FOREIGN PATENT DOCUMENTS

| CN | 205729898 | 11/2016 |
| --- | --- | --- |
| CN | 206508345 | 9/2017 |
| DE | 612248 | 4/1935 |
| FR | 488379 | 9/1918 |
| JP | S58-137883 | 9/1983 |
| JP | 2011-518986 | 6/2011 |
| JP | 2015-536742 | 12/2015 |
| WO | WO 2014/090745 | 6/2014 |
| WO | WO 2014/152704 | 9/2014 |

OTHER PUBLICATIONS

PCT International Search Report and Written Opinion in Application No. PCT/EP2018/078684, dated Feb. 13, 2019, 11 pages.
PCT International Preliminary Report on Patentability in Application No. PCT/EP2018/078684, dated Apr. 21, 2020, 7 pages.

* cited by examiner

MEDICAL PUMP

CROSS REFERENCE TO RELATED APPLICATIONS

The present application is the national stage entry of International Patent Application No. PCT/EP2018/078684, filed on Oct. 19, 2018, and claims priority to Application No. EP 17306415.5, filed on Oct. 19, 2017, the disclosures of which are incorporated herein by reference.

TECHNICAL FIELD

The present disclosure relates to a medical pump and to a method of operating a medical pump.

BACKGROUND

Medical pumps are capable of displacing medicament and/or bodily fluid. The medical pump may comprise a void into which a liquid is drawn. The liquid is then expelled from the void for delivery to a patient.

SUMMARY

It is an object of the present disclosure to provide an improved medical pump.

According to the present disclosure, there is provided a medical pump comprising a medical pump for dispensing a liquid, the medical pump comprising: a housing comprising an inlet for receiving said liquid and an outlet for dispensing said liquid; a receptacle comprising a chamber and a passage that is in fluid communication with the chamber, wherein the receptacle is received in the housing and is axially movable relative to the housing from a filling position, wherein the passage fluidly communicates the chamber with the inlet, to a dispensing position, wherein the passage fluidly communicates the chamber with the outlet; and, a piston that is received in the chamber and is configured such that when the receptacle is in the filling position the piston is axially moveable relative to the receptacle to draw said liquid from the inlet into the chamber and when the receptacle is in the dispensing position the piston is axiallymoveable relative to the receptacle to dispense liquid in the chamber through the outlet.

In one embodiment, the receptacle is lockable relative to the housing to prevent axial movement of the receptacle relative to the housing.

The receptacle and piston may be configured to move together relative to the housing when the receptacle moves to the filling position and to the dispensing position.

The receptacle may comprise a peripheral wall that extends about the chamber. The passage may extend through the peripheral wall of the receptacle.

In one embodiment, wherein the housing comprises a peripheral wall that extends about the receptacle received in the housing. The inlet and outlet may each comprise a respective aperture in the peripheral wall of the housing.

In one embodiment, the housing further comprises an opening, wherein the receptacle is axially movable relative to the housing to a third position wherein the passage fluidly communicates the chamber with the opening, and wherein the piston is configured such that when the receptacle s in the third position the piston is axially moveable relative to the receptacle to induce a flow of liquid between the chamber and opening.

In one embodiment, the housing further comprises a second inlet for receiving a second liquid, wherein the receptacle is axially movable relative to the housing to a second filling position wherein the passage fluidly communicates the chamber with the second inlet, the piston configured such that when the receptacle is in the second filling position the piston is axially moveable relative to the receptacle to draw said second liquid into the chamber from the second inlet.

In one embodiment, the housing further comprises a second outlet, wherein the receptacle is axially movable relative to the housing to a second dispensing position wherein the passage fluidly communicates the chamber with the second outlet, the piston configured such thatwhen the receptacle is in the second dispensing position the piston is axially moveable relative to the receptacle to dispense liquid contained in the chamber through the second outlet.

In one embodiment, the medical pump further comprises a detection mechanism configured to determine whether the contents of the chamber fulfils a predetermined compression property requirement, wherein the medical pump is configured such that the receptacle is moved to the second dispensing position and then the receptacle and piston are moved relative to each other to dispense liquid in the chamber through the second outlet if the predetermined compression property requirement is not fulfilled.

In one embodiment, the receptacle is moveable to a detection position wherein the chamber is not fluidly communicated with any of the inlet, outlet and second outlet, and wherein the detection mechanism is configured to move the receptacle and piston relative to each other when the receptacle is in the detection position to detect information indicative of whether the contents of the chamber fulfils said predetermined compression property requirement.

The medical pump may further comprise a sensor unit configured to detect information indicative of a property of liquid expelled from the chamber.

In one embodiment, the medical pump further comprises an occlusion detection mechanism configured to determine whether a drug delivery site of a patient's body exceeds a predetermined occlusion property. In one such embodiment, the medical pump further comprises an alarm that is operated if the occlusion detection mechanism determines that the drug delivery site exceeds said predetermined occlusion property. Alternatively, or additionally, the occlusion detection mechanism may be configured to prevent the delivery of medicament to the drug delivery site if the occlusion detection mechanism determines that the drug delivery site exceeds said predetermined occlusion property.

The inlet may be connected to a medicament source comprising a medicament. The medicament source may comprise a flexible bag containing the medicament.

According to the present disclosure, there is also provided a method of operating a medical pump, the medical pump comprising: a housing having an inlet and an outlet; a receptacle having a chamber and a passage that is in fluid communication with the chamber; and, a piston that is received in the chamber, the method comprising: providing the receptacle in a filling position within the housing wherein the passage fluidly communicates the chamber with the inlet; moving the piston axially relative to the receptacle to draw liquid into the chamber from the inlet whilst the receptacle is in the filling position, moving the receptacle axially relative to the housing to a dispensing position wherein the passage fluidly communicates the chamber with the outlet; and, moving the piston axially relative to the receptacle to dispense liquid in the chamber through the outlet whilst the receptacle is in the dispensing position.

These and other aspects will be apparent from and elucidated with reference to the embodiments described hereinafter.

BRIEF DESCRIPTION OF THE FIGURES

Embodiments of the disclosure will now be described, by way of example only, with reference to the accompanying drawings, in which.

DETAILED DESCRIPTION

Figure 1:
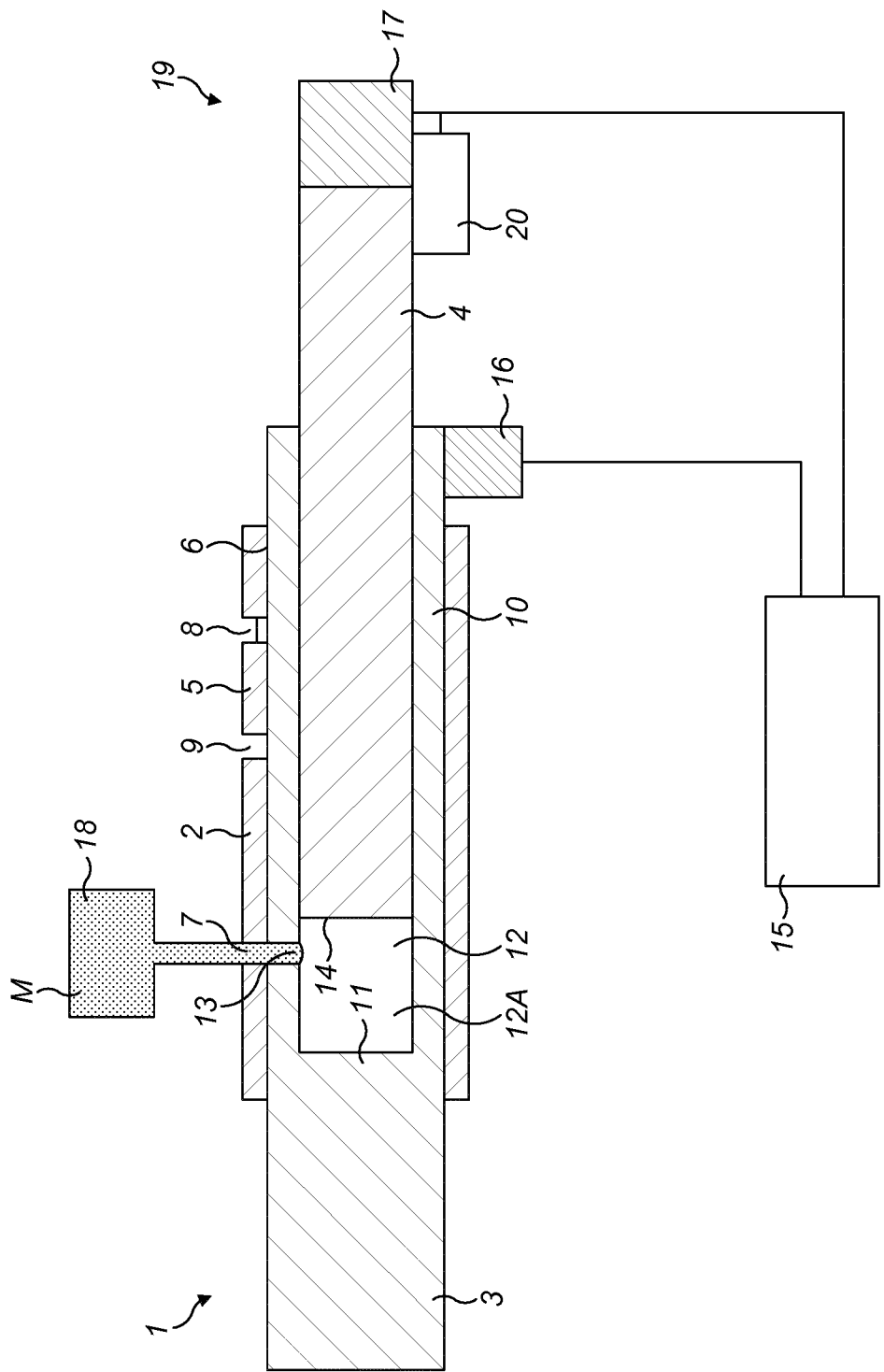
FIG. 1 is schematic cross-sectional view of a medical pump according to a first embodiment of the disclosure.

A medical pump, as described herein, may be configured to deliver a medicament to a patient. For example, delivery could be sub-cutaneous, intra-muscular, or intravenous. Such a device could be operated by a patient or care-giver, such as a nurse or physician, and can include various types of medical pump. Additionally, or alternatively, the medical pup may be configured to withdraw a bodily fluid from a patient or from a bodily fluid source such as a pre-filled container of bodily fluid.

The medical pumps described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Pumps can further include gears, valves, or other mechanisms to convert energy into movement of one or more components of a device.

The one or more automated functions of a medical pump may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some medical pumps can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Referring now to FIGS. 1 to 9, a medical pump 1 according to first embodiment of the disclosure is shown. The medical pump 1 comprises a housing 2, a receptacle 3 and a piston 4.

The housing 2 comprises a peripheral wall 5 and a receptacle receiving space 6. The peripheral wall 5 is generally annular. The peripheral wall 5 subtends about the receptacle receiving space 6 such that the housing 2 is open ended.

The housing 2 comprises an inlet 7 and first and second outlets 8, 9. The inlet 7 and first and second outlets 8, 9 each comprise a respective opening in the peripheral wall 5. The opening may be an aperture through the peripheral wall 5. The inlet 7 and first and second outlets 8, 9 are spaced in the direction of the central axis (shown by the dashed line 'A-A' in FIG. 4) of the receptacle 3.

The receptacle 3 is received in the receptacle receiving space 6 of the housing 2. The receptacle 3 is axially slidable relative to the housing 2. The receptacle 3 comprises a peripheral wall 10 and an end wall 11 that together define a chamber 12. The receptacle 3 may be generally cylindrical to correspond to the generally cylindrical receptacle receiving space 6. The peripheral wall 10 of the receptacle 3 is generally annular. The peripheral wall 10 of the receptacle 3 extends about the chamber 12.

The receptacle 3 comprises a passage 13 that is fluidly communicated with the chamber 12. In the present embodiment, the passage 13 extends radially through the peripheral wall 10 of the receptacle 3 and may comprise an aperture. However, in an alternative embodiment (not shown), the passage 13 extends through at least a portion of the end wall 11. In one such embodiment (not shown), the passage 13 extends axially from the chamber 12 through a portion of the end wall 11 and then extends radially to the exterior of the receptacle 3.

The receptacle 3 is slidable relative to the housing 2 to selectively align the passage 13 with the inlet 7 and first and second outlets 8, 9 to fluidly communicate therewith, as is described in more detail below.

The receptacle 3 has an open end that is remote to the end wall 11 and is configured to receive the piston 4 such that an end 14 of the piston 4 is received in the chamber 12. The piston 4 is axially moveable relative to the receptacle 3. More specifically, the piston 4 is slidable relative to the receptacle 3 in a first direction (shown by arrow 'X' in FIG. 4), wherein the piston 4 is moved axially away from the end wall 11 of the receptacle 3, and a second direction (shown by arrow 'Y' in FIGS. 6 and 7), wherein the piston 4 is moved axially towards the end wall 11 of the receptacle 3.

The piston 4 is generally cylindrical to correspond to the generally cylindrical chamber 12 of the receptacle. The piston 4 is generally elongate. The piston 4 is generally rod-shaped. However, it should be recognised that in alternative embodiments (not shown) the piston 4 and chamber 12 may be a shape other than cylindrical, for example, having a square, triangular or rectangular cross-section. Similarly, the receptacle 3 and receptacle receiving space 6 of the housing 2 may be a shape other than cylindrical, for example, having a square, triangular or rectangular cross-section.

The housing 2, receptacle 3 and piston 4 are moveable along a common axis A-A.

The medical pump 1 further comprises an actuator unit and a controller 15. The controller 15 is configured to control operation of the actuator unit. The controller 15 may be connected to an input device (not shown), for example, one or more buttons or switches. The actuator unit comprises first and second actuators 16, 17 that comprise first and second motors 16A, 17B respectively.

In some embodiments, the first and second motors 16A, 17B comprise rotary motors that drive respective gear assemblies to urge the receptacle 3 and piston 4 in a linear motion relative to the housing 2 in the first direction X and second direction Y.

Figure 2:
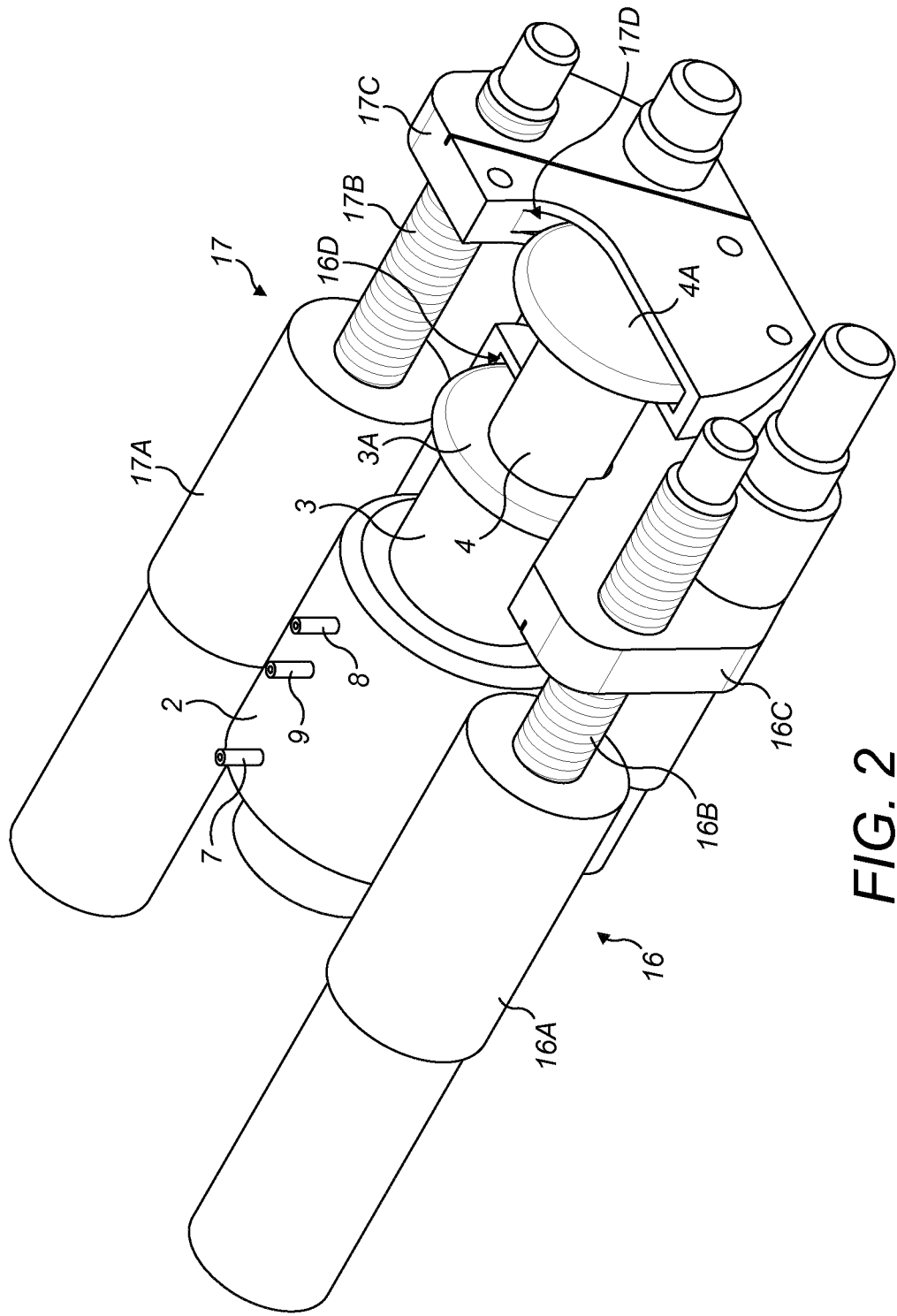
FIG. 2 is a perspective view of part of the medical pump of FIG. 1.

In the present embodiment, the first motor 16A is configured to rotate a first threaded shaft 16B. A first drive member 16C is coupled to the first threaded shaft 16B such that rotation of the first threaded shaft 16B causes linear movement of the first drive member 16C. For example, the first drive member 16C may comprise a threaded aperture that receives the first threaded shaft 16B. The first drive member 16C is coupled to the receptacle 3 such that linear movement of the first drive member 16C results in corresponding movement of the receptacle 3. In the present embodiment, the receptacle 3 comprises a flange 3A that extends radially outwardly from an end of the receptacle 3. The first drive member 16C comprises a slot 16D that receives at least a portion of the flange 3A of the receptacle 3 such that the receptacle 3 and first drive member 16C are coupled together (as shown in FIG. 2). The engagement of the flange 3A in the slot 16D fixes the receptacle 3 relative to the first drive member 16C in the direction of the central axis A-A. However, the slot 16D allows for the receptacle 3 to be removed from the first drive member 16C in the radial direction. More specifically, the user can remove the receptacle 3 from the first drive member 16C by lifting the receptacle 3 out of the slot 16D in the first drive member 16C. Therefore, the user is able to detach the receptacle 3 from the first drive member 16C to dispose of the receptacle 3 whilst retaining the first motor 16A. This is advantageous because the receptacle 3, which has been in contact with the medicament M, can be safely disposed of whist the relatively complex/expensive first motor 16A and controller 15 can be reused.

The second motor 17A is configured to rotate a second threaded shaft 17B. A second drive member 17C is coupled to the second threaded shaft 17B such that rotation of the second threaded shaft 17B causes linear movement of the second drive member 17C. For example, the second drive member 17C may comprise a threaded aperture that receives the second threaded shaft 17B. The second drive member 17C is coupled to the piston 4 such that linear movement of the second drive member 17C results in corresponding movement of the piston 4. In the present embodiment, the piston 4 comprises a flange 4A that extends radially outwardly from an end of the piston 4. The second drive member 17C comprises a slot 17D that receives at least a portion of the flange 4A of the piston 4 such that the piston 4 and second drive member 17C are coupled together (as shown in FIG. 2). The engagement of the flange 4A in the slot 17D fixes the piston 4 relative to the second drive member 17C in the direction of the central axis A-A. However, the slot 17D allows for the piston 4 to be removed from the second drive member 17C in the radial direction. More specifically, the user can remove the piston 4 from the second drive member 17C by lifting the piston 4 out of the slot 17D in the second drive member 17C. Therefore, the user is able to detach the piston 4 from the second drive member 17C to dispose of the piston 4 whilst retaining the second motor 17A. This is advantageous because the receptacle 3, which has been in contact with the medicament M, can be safely disposed of whist the relatively complex/expensive second motor 17A and controller 15 can be reused.

In some embodiments, the housing 2 may also be disposed of. In one such embodiment, the housing 2, receptacle 3 and piston 4 are removable together to be disposed of. A new replacement housing 2, receptacle 3 and piston 4 may then be installed by arranging the piston 4 within the receptacle 3, and the receptacle 3 within the housing 2, and then slotting the flange 3A of the receptacle 3 into the slot 16D of the first drive member 16C and slotting the flange 4A of the piston 4 into the slot 17D of the second drive member 17C.

The receptacle 3 and piston 4 each comprise first and second ends, wherein the first ends are located at a first side of the medical pump 1 and the second ends are located at a second side of the medical pump 1. The actuators 16, 17 may be configured to act on the respective first ends of the receptacle 3 and piston 4, or to act on the respective second ends of the receptacle 3 and piston 4. This allows the medical pump 1 to be made more compact in comparison to configurations wherein the first actuator 16 acts on a first end of the receptacle 3 and the second actuator 17 acts on a second end of the piston 4 that is on the opposite side of the medical pump 1 to the first end of the receptacle 3.

In an alternative embodiment (not shown), the first and second motors 16A, 17A are coupled to respective pinion gears (not shown) and the receptacle 3 and piston 4 are coupled to respective rack gears (not shown). Operation of the first motor 16A rotates the corresponding pinon gear to drive the linear gear axially, which results in axial movement of the receptacle 3 relative to the housing 2. Operation of the second motor 17A rotates the corresponding pinion gear to drive the linear gear axially, which results in axial movement of the piston 4 relative to the housing 2. In another embodiment (not shown), the first and second actuators 16, 17 comprise a different type of actuator, for instance, a linear solenoid. In yet another embodiment (not shown), the actuator unit comprises a single actuator, for example, a single motor, that drives both the receptacle 3 and piston 4 relative to the housing 2. For example, the single actuator may be coupled to a gearbox (not shown) that is configured to independently drive each of the receptacle 3 and piston 4.

In an alternative embodiment (not shown), the first and second motors 16A, 17A comprise linear motors, having a stator (not shown) and a linear rotor (not shown). The linear rotor of the first motor is coupled to the receptacle 3 and the linear rotor of the second motor is coupled to the piston 4. The first motor is operable to drive the linear rotor of the first motor relative to the stator to move the receptacle 3 axially relative to the housing 2. The second motor is operable to drive the liner rotor of the second motor relative to the stator to move the piston 4 axially relative to the housing 2. Thus, the first and second motors are operable to move the receptacle 3 and piston 4 in a linear reciprocal motion relative to the housing 2.

The medical pump 1 is configured such that the receptacle 3 may be locked in position relative to the housing 2 to prevent axial movement of the receptacle 3 relative to the housing 2. In some embodiments, the actuator unit performs the function of locking the receptacle 3 relative to the housing 2. For example, the first actuator 16 may be operated to hold the receptacle 3 in position relative to the housing 2. In one such embodiment, the first actuator 16 comprises a stepper motor that is configured to exert a holding torque on the receptacle 3 to lock the receptacle 3 in position relative to the housing 2. In another embodiment (not shown), the medical pump 1 further comprises a locking mechanism (not shown) that is configured to lock the receptacle 3 in position relative to the housing 2. For example, one of the housing 2 and receptacle 3 may comprise a locking member (not shown) that is moveable from an unlocked state to a locked state wherein the locking member engages with the other one of the housing 2 and receptacle 3 to hold the receptacle 3 in an axial position relative to the housing 2.

Alternatively, or additionally, the medical pump 1 is configured such that the piston 4 may be locked in position relative to the housing 2 to prevent axial movement of the piston 4 relative to the housing 2. In some embodiments, the actuator unit performs the function of locking the piston 4 relative to the housing 2. For example, the second actuator 17 may be operated to hold the piston 4 in position relative to the housing 2. In one such embodiment, the second actuator 17 comprises a stepper motor that is configured to exert a holding torque on the piston 4 to lock the piston 4 in position relative to the housing 2. In another embodiment, the medical pump 1 further comprises a locking mechanism (not shown) that is configured to lock the piston 4 in position relative to the housing 2. For example, one of the housing 2 and piston 4 may comprise a locking member (not shown) that is moveable from an unlocked state to a locked state wherein the locking member engages with the other one of the housing 2 and piston 4 to hold the piston 4 in an axial position relative to the housing 2.

A medicament source 18 is fluidly connected to the inlet 7 of the housing 2. The medicament source 18 comprises a reservoir containing medicament M. In one embodiment (not shown), the reservoir comprises a flexible bag that contains the medicament M. The reservoir may be connected to the inlet 7 of the housing 2 by a conduit (not shown), for example, a flexible tube.

The first outlet 8 is fluidly connected to a medicament delivery member (not shown), for example, a needle or flexible tubing, that is configured to deliver medicament from the first outlet 8 to the user's body. For instance, the medicament delivery member may comprise a needle that is inserted into an injection site of the user such that the medicament M is delivered to the injection site. The second outlet 9 is fluidly connected to a container (not shown) for receiving medicament expelled from the second outlet 9.

In some embodiments, the inlet 7 is detachable from the medicament source 18, the first outlet 8 is detachable from the medicament delivery member and the second outlet 9 is detachable from the container for receiving medicament. Thus, the housing 2 may be disposed of separately to the medicament source 18, medicament delivery member and container for receiving medicament.

The medical pump 1 further comprises a detection mechanism 19 configured to determine whether the contents of the chamber 12 fulfils a predetermined compression property requirement, as will be described in more detail below. In the present embodiment, the detection mechanism 19 comprises the controller 15, the first and/or second actuator 16, 17 of the actuator unit, and a sensor 20. The sensor 20 is configured to detect information indicative of whether the contents of the chamber 12 fulfils a predetermined compression requirement.

In an alternative embodiment, the controller 15 and first and second actuators 16, 17 do not form part of the detection mechanism 19 and instead the detection mechanism 19 comprises a further controller (not shown) and further actuator (not shown). The further actuator may be configured to move at least one of the receptacle 3 and piston 4 relative to the other one of the receptacle 3 and piston 4 when the detection mechanism 19 is operated to determine whether the contents of the chamber 12 fulfils said predetermined compression requirement.

The medical pump 1 is configured to draw medicament from the medicament source 18 into the chamber 12. If the medicament drawn into the chamber 12 fulfils said predetermined compression property requirement then the medicament is expelled from the chamber 12 through the first outlet 8 of the housing 2 such that the medicament is delivered to the user via the medicament delivery member. If the medicament drawn into the chamber 12 does not fulfil said predetermined compression property requirement then the medicament is expelled from the chamber 12 through the second outlet 9 of the housing 2 to be collected in the container, such that the expelled medicament can be disposed of.

Figure 3:
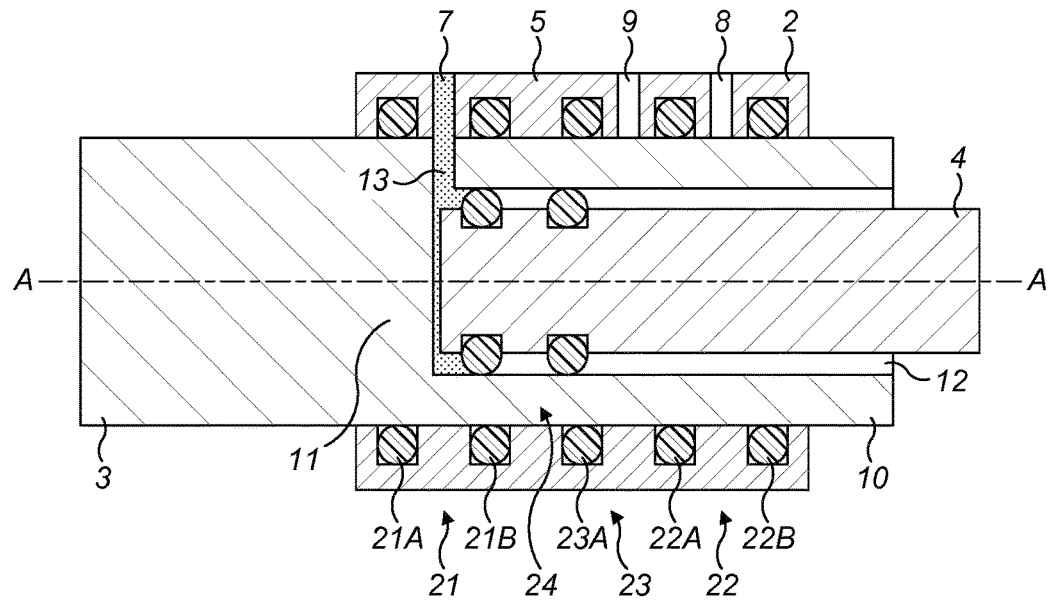
FIG. 3 is a schematic cross-sectional view of part of a housing, receptacle and piston of the medical pump of FIG. 1, wherein the receptacle is in a filling position.

An exemplary operation of the medical pump 1 will now be described with reference to FIGS. 3 to 7. For the sake of clarity only, not all of the components of the medical pump 1 are shown in the FIGS. 3 to 7. The receptacle 3 is initially in a filling position and the end 14 of the piston 4 abuts the end wall 11 of the receptacle 3 (as shown in FIG. 3). When the receptacle 3 is in the filling position, the passage 13 of the receptacle 3 fluidly communicates the chamber 12 with the inlet 7.

Figure 4:
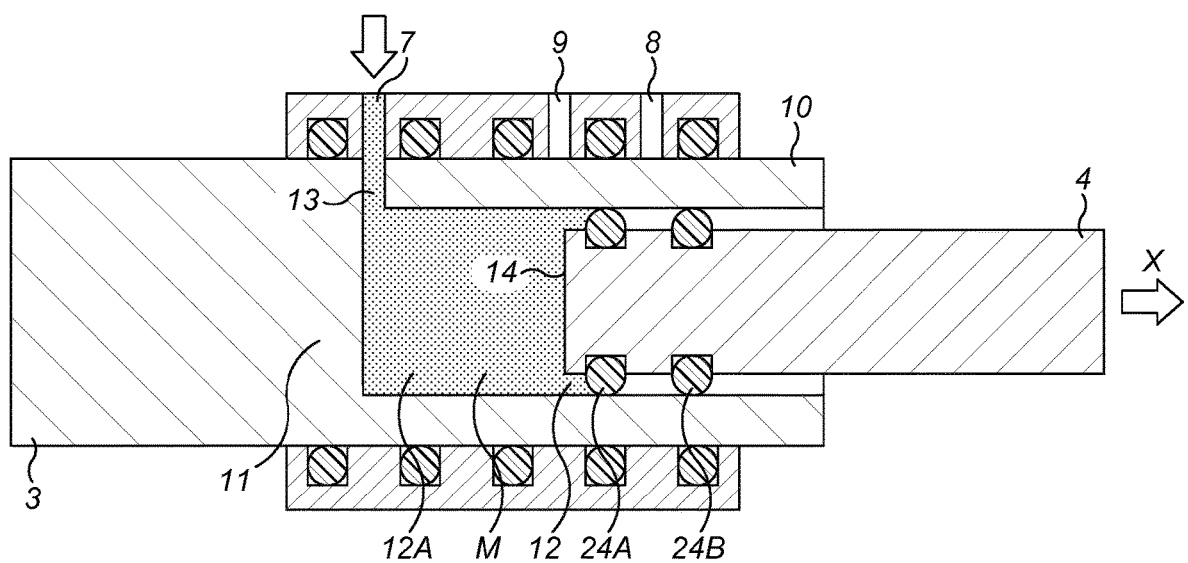
FIG. 4 is a schematic cross-sectional view of the housing, receptacle and piston of FIG. 3, wherein the receptacle is in the filling position and liquid is drawn into the receptacle.

With the receptacle 3 in the filling position, the second actuator 17 is then operated to move the piston 4 axially in the first direction X relative to the housing 2 and receptacle 3. This causes the end 14 of the piston 4 to move away from the end wall 11 of the receptacle 3 such that a space 12A is formed therebetween (as shown in FIG. 4). The movement of the piston 4 in the first direction X creates a suction effect that causes medicament M from the medicament source 18 to be drawn into the chamber 12, via the inlet 7 and passage 13, to fill the space 12A. In some embodiments, the receptacle 3 is axially locked relative to the housing 2 whilst the piston 4 is moved to draw medicament M into the chamber 12. The amount of medicament M drawn into the chamber 12 may correspond to a dose of medicament M. The medicament source 18 may contain a plurality of doses of medicament M. The distance that the piston 4 is moved in the first direction X relative to the receptacle 3 may be adjusted to vary the amount of medicament M that is drawn into the chamber 12. In one such embodiment, the user may input a dosage into the controller 15 using an input device and the controller 15 operates the second actuator 17 accordingly to draw the desired volume of medicament M into the chamber 12. It should be recognised that in an alternative embodiment (not shown), the receptacle 3 may be moved relative to the housing 2 and piston 4 to draw medicament into the chamber 12. In such an embodiment, the inlet 7 and passage 13 must be shaped to remain in fluid communication during relative movement of the receptacle 3 and housing 4, for example, the inlet 7 may have sufficient dimension in the axial direction such that the passage 13 remains in fluid communication therewith.

Figure 5:
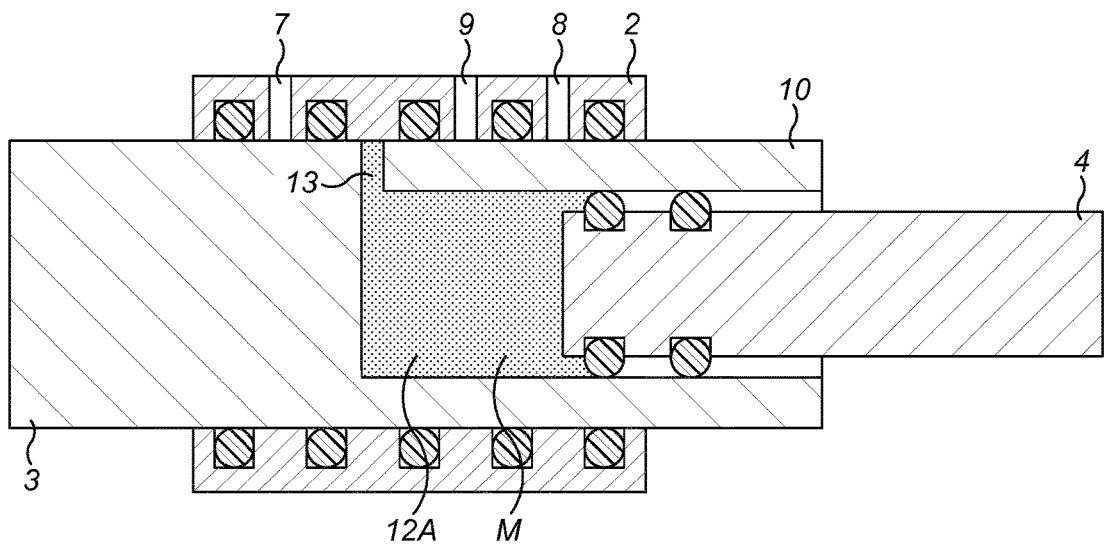
FIG. 5 is a schematic cross-sectional view of the housing, receptacle and piston of FIG. 3, wherein the receptacle is in a detection position.

The receptacle 3 is then moved to a detection position (as shown in FIG. 5), wherein the passage 13 of the receptacle 3 is not aligned with any of the inlet 7 and first and second outlets 8, 9. Thus, the medicament M contained in the space 12A of the chamber 12 is not fluidly communicated with any of the inlet 7 and first and second outlets 8, 9 and instead the space 12A is sealed. In some embodiments, the passage 13 is blocked by an inner surface of the peripheral wall 5 of the housing 2 when the receptacle 3 is in the detection position.

To move the receptacle 3 to the detection position, the first actuator 16 is operated to move the receptacle 3 axially in the first direction X relative to the housing 2. The piston 4 also moves by the same distance in the first direction X such that the relative position of the receptacle 3 with respect to the piston 4 is unchanged. In one embodiment, movement of the receptacle 3 in the first direction X relative to the housing 2 causes corresponding movement of the piston 4 relative to the housing 2 because the medicament M in the space 12A is urged against the end 14 of the piston 4. In an alternative embodiment, the second actuator 17 is operated at the same time as the first actuator 16 such that the receptacle 3 and piston 4 are moved together in the first direction X relative to the housing 2 under the force of the respective first and second actuators 16, 17.

With the receptacle 3 in the detection position, the detection mechanism 19 is operated to determine whether the contents of the chamber 12 fulfils a predetermined compression property requirement. In more detail, the second actuator 17 is operated to urge the piston 4 in the second direction Y relative to the receptacle 3 and the receptacle 3 is held axially stationary relative to the housing 2. This causes the medicament M received in the space 12A to be compressed. In some embodiments, the second actuator 17 applies a predetermined force to the piston 4 to urge the piston 4 in the second direction Y relative to the receptacle 3 and the sensor 20 is configured to detect the resultant displacement of the piston 4 in the second direction Y. The greater the compressibility of the contents of chamber 12, the larger the distance that the piston 4 will move in the second direction Y.

The sensor 20 may comprise, for example, a proximity sensor that is mounted to the piston 4 and detects the distance to a point on the medical pump 1, for instance, a point on the housing 2 or receptacle 3. Alternatively, the proximity sensor may be mounted to a point on the medical pump 1, for instance, the housing 2 or receptacle 3, and detects the distance to the piston 4. Thus, by measuring the change in the distance between the piston 4 and said point on the medical pump 1, the distance of travel of the piston 4 can be detected. The proximity sensor may be an optical proximity sensor. In other embodiments (not shown), the sensor 20 comprises one or more of a capacitive sensor, Doppler effect sensor, Eddy-current sensor, magnetic sensor, Hall-effect sensor or ultrasonic sensor. In one embodiment (not shown), the sensor 20 is configured to detect rotation of a rotor of the second actuator 17 to determine the distance of travel of the piston 4. In yet another embodiment (not shown), the sensor 20 comprises a switch that is closed if the piston 4 moves in the second direction Y by greater than a predetermined distance.

In alternative embodiments (not shown), the a predetermined force is applied to the receptacle 3 to urge the receptacle 3 in the first direction X relative to the piston 4 and the piston 4 is held axially stationary relative to the housing 2. The sensor 20 may be configured to detect the resultant displacement of the receptacle 3 in the first direction X. In one embodiment (not shown), the detection mechanism 19 comprises the first actuator 16, which is operated to urge the receptacle 3 in the first direction X relative to the piston 4.

The detection of whether the contents of the space 12A of the chamber 12 fulfils the predetermined compression property requirement allows for the detection mechanism 19 to assess whether gas or gas bubbles are present in the space 12A in the chamber 12 along with the medicament M. Such gas may have entered the chamber 12 during the introduction of the medicament M, due to leakage or gas bubbles that were present in the medicament source 18.

The relative movement of the receptacle 3 and piston 4 when the receptacle 3 is in the detection position compresses the contents of the space 12A. The predetermined compression property requirement is fulfilled if the contents of the space 12A is compressed by less than a predetermined amount. As discussed above, this predetermined amount may relate to the distance that the piston 4 is moved relative to the receptacle 3 when the receptacle 3 is in the detection position and the corresponding actuator 16, 17 is operated.

Alternatively, the predetermined amount of compression may relate to a defined volume of the space 12A to which the contents of the space 12A may just be compressed when no hazardous amount of gas is present in the space 12A. As said volume depends on the force or the pressure by which the receptacle 3 and chamber 4 are moved relatively towards each other, the compression of the medicament M in the space 12A may be carried out at a given force or pressure exerted on the receptacle 3 or piston 4 to cause relative movement of the receptacle 3 and piston 4. Similarly, as discussed above, the predetermined amount may relate or be determined by the axial distance by which receptacle 3 and piston 4 are moved relative to each other at a given force. Alternatively, the predetermined amount of compression may relate or be determined via the force necessary to move one of the receptacle 3 and piston 4 a given axial distance towards the other one of the receptacle 3 and piston 4. Said given axial distance would then define a given size or volume of the space 12A in the chamber 12.

If a critical or hazardous amount of gas is present in the space 12A, the contents of the space 12A is compressed more than the predetermined amount upon relative movement of the receptacle 3 and piston 4. This is due to a greater compressibility of the contents of the space 12A because gas has a compressibility which is greater than that of liquid. Depending on the speed of relative movement of the receptacle 3 and piston 4, the compressibility may be the isothermal compressibility or the adiabatic compressibility.

Said distance, volume or force may be monitored by the controller 15 or an additional element or gauge of the medical pump 1 during the operation of the detection mechanism 19. To this effect, the controller 15 may compare the respective variable chosen from distance, volume or force, as mentioned above, to a threshold value which is stored by the controller 15 and separates acceptable values of the respective variable from non-acceptable values. For example, if said distance or volume which is reached during the operation of the detection mechanism 19 is equal to or greater than the threshold value, then, the predetermined compression property requirement is fulfilled, as the contents of the chamber 12 is not compressed up to the predetermined amount. When, in this regard, said distance or volume which is reached during the operation of the detection mechanism 19 is smaller than the predetermined extent, then, the predetermined compression property requirement is not fulfilled, as the contents of the chamber 12 is compressed to a value greater than the predetermined amount. If the predetermined amount of compression is determined by said force, then, the predetermined compression property requirement is fulfilled for forces equal to or greater than the threshold value. Accordingly, the predetermined compression property requirement is not fulfilled for forces smaller than the threshold value.

Figure 6:
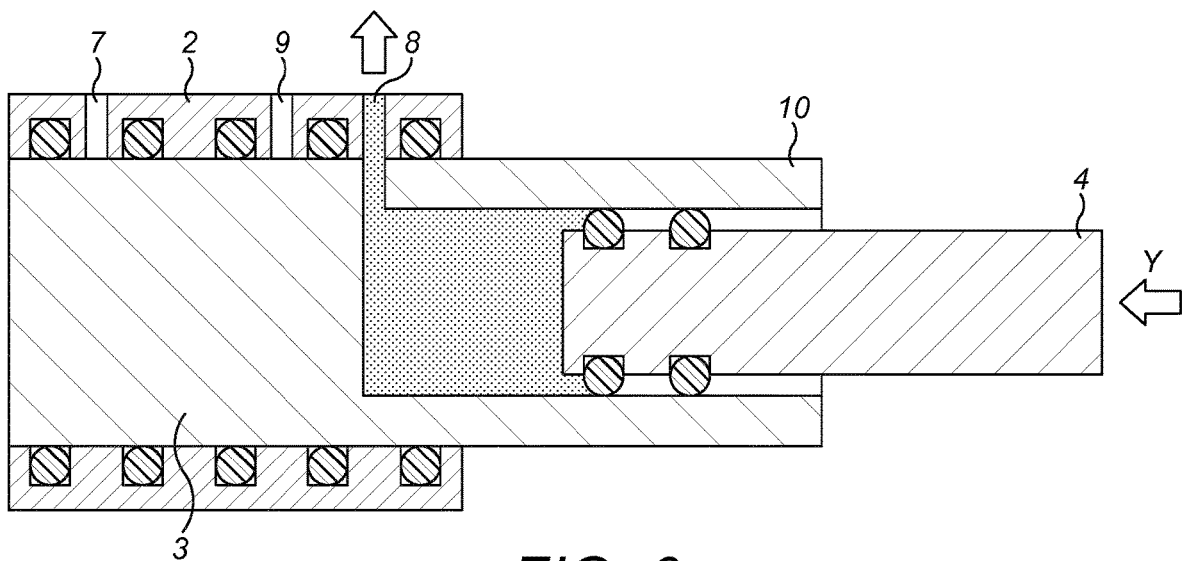
FIG. 6 is a schematic cross-sectional view of a housing, receptacle and piston of FIG. 3, wherein the receptacle is in a first dispensing position.

If the detection mechanism 19 determines that the chamber 12 is sufficiently free of gas that the predetermined compression property requirement is fulfilled, then the receptacle 3 is moved relative to the housing 2 to a first dispensing position wherein the passage 13 of the receptacle 3 is aligned with the first outlet 8 (see FIG. 6). Thus, the medicament M in the chamber 12 is fluidly communicated with the first outlet 8 via the passage 13.

To move the receptacle 3 to the first dispensing position, the first actuator 16 is operated to move the receptacle 3 axially in the first direction X relative to the housing 2. The piston 4 also moves by the same distance in the first direction X such that the relative position of the receptacle 3 with respect to the piston 4 is unchanged. In one embodiment, movement of the receptacle 3 in the first direction X relative to the housing 2 to the first dispensing position causes corresponding movement of the piston 4 relative to the housing 2 because the medicament M in the space 12A is urged against the end 14 of the piston 4. In an alternative embodiment, the second actuator 17 is operated at the same time as the first actuator 16 such that the receptacle 3 and piston 4 are moved together in the first direction X relative to the housing 2 under the force of the respective first and second actuators 16, 17.

With the receptacle 3 in the first dispensing position, the second actuator 17 is operated to move the piston 4 axially in the second direction Y relative to the housing 2 and receptacle 3. This causes the end 14 of the piston 4 to move towards the end wall 11 of the receptacle 3 such that size of the space 12A reduces and thus medicament M in the chamber 12 is expelled out of the passage 13 in the receptacle 3 and dispensed through the first outlet 8. Thus, the medicament M in the space 12A is delivered to the user's body via the medicament delivery member. In some embodiments, the receptacle 3 is axially locked relative to the housing 2 whilst the piston 4 is moved to expel medicament from the chamber 12. The medicament M may be expelled from the chamber 12 until the end 14 of the piston 4 abuts the end wall 11 of the receptacle 3. In an alternative embodiment, the receptacle 3 is moved relative to the housing 2 and piston 4 to expel medicament from the chamber 12.

Once the medicament M has been expelled from the chamber 12, the receptacle 3 is moved from the first dispensing position to the filling position (shown in FIG. 3) and the above process may be repeated. With the receptacle 3 returned to the filing position, the piston 4 is again moved relative to the receptacle 3 to draw further medicament M into the chamber 12 from the medicament source 18.

Figure 7:
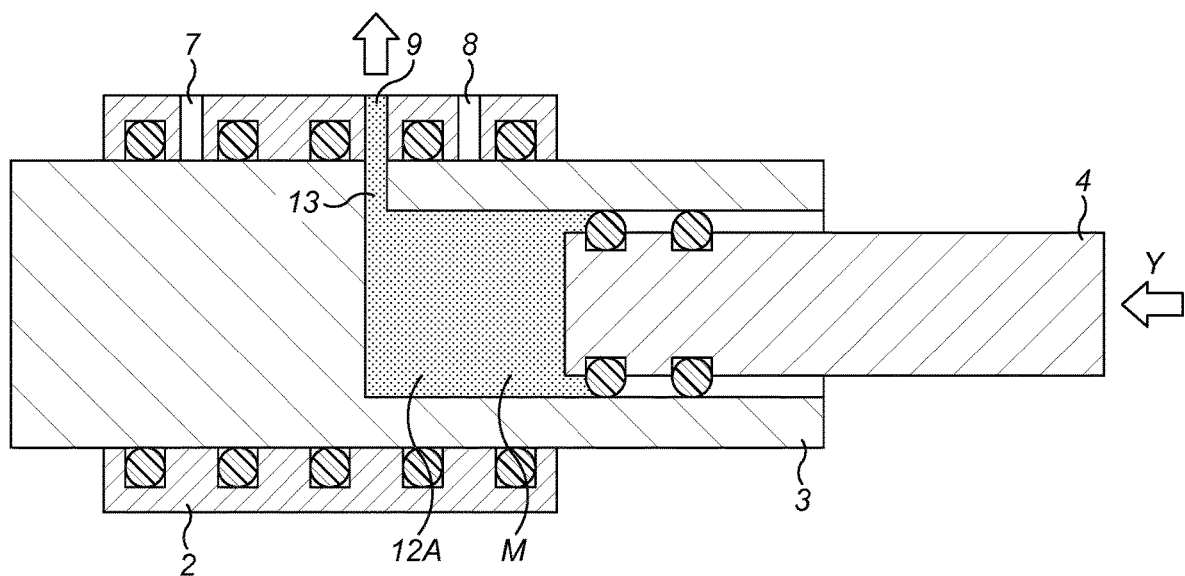
FIG. 7 is a schematic cross-sectional view of a housing, receptacle and piston of FIG. 3, wherein the receptacle is in a second dispensing position.

If the detection mechanism 19 determines that the chamber 12 contains sufficient gas that the predetermined compression property requirement is not fulfilled, then the receptacle 3 is moved relative to the housing 2 to a second dispensing position wherein the passage 13 of the receptacle 3 is aligned with the second outlet 9 (see FIG. 7). Thus, the medicament M in the chamber 12 is fluidly communicated with the second outlet 9 via the passage 13.

To move the receptacle 3 to the second dispensing position, the first actuator 16 is operated to move the receptacle 3 axially in the first direction X relative to the housing 2. The piston 4 also moves by the same distance in the first direction X such that the relative position of the receptacle 3 with respect to the piston 4 is unchanged. In one embodiment, movement of the receptacle 3 in the first direction X relative to the housing 2 to the second dispensing position causes corresponding movement of the piston 4 relative to the housing 2 because the medicament M in the space 12A is urged against the end 14 of the piston 4. In an alternative embodiment, the second actuator 17 is operated at the same time as the first actuator 16 such that the receptacle 3 and piston 4 are moved together in the first direction X relative to the housing 2 under the force of the respective first and second actuators 16, 17.

With the receptacle 3 in the second dispensing position, the second actuator 17 is operated to move the piston 4 axially in the second direction Y relative to the housing 2 and receptacle 3. This causes the end 14 of the piston 4 to move towards the end wall 11 of the receptacle 3 such that the size of the space 12A reduces and thus medicament M in the chamber 12 is expelled out of the passage 13 in the receptacle 3 and through the second outlet 9. Thus, the medicament M in the space 12A is delivered to the container (not shown) that is fluidly connected to the second outlet 9. Thus, the medicament M, which may comprise gas in a quantity that is hazardous if delivered to the human body, may be safely disposed of. In some embodiments, the receptacle 3 is axially locked relative to the housing 2 whilst the piston 4 is moved to expel medicament from the chamber 12. The medicament M may be expelled from the chamber 12 until the end 14 of the piston 4 abuts the end wall 11 of the receptacle 3. In an alternative embodiment, the receptacle 3 is moved relative to the housing 2 and piston 4 to expel medicament from the chamber 12.

Once the medicament M has been expelled from the chamber 12, the receptacle 3 is moved from the second dispensing position to the filling position (shown in FIG. 3) and the above process may be repeated. With the receptacle 3 returned to the filing position, the piston 4 is again moved relative to the receptacle 3 to draw further medicament M into the chamber 12 from the medicament source 18.

Figure 8:
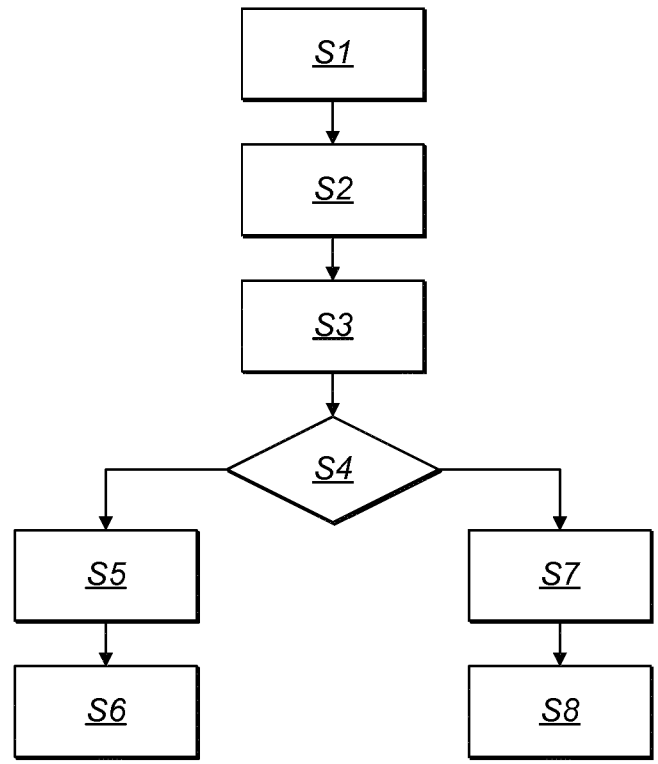
FIG. 8 is a flow diagram illustrating a method of operation of the medical pump.

A flow diagram illustrating a method of operation of the medical pump 1 is shown in FIG. 8. In some embodiments, one or more of the steps S1 to S8 are carried out by the controller 15. At step S1, the receptacle 3 is located in the filling position and the piston 4 is located such that the end 14 of the piston 4 abuts the end wall 11 of the receptacle 3. At step S2, the piston 4 is moved relative to the receptacle 3 to draw medicament M into the chamber 12 from the inlet 7. At step S3, the receptacle 3 and piston 4 are moved together relative to the housing 2 such that the receptacle is moved to the detection position. At step S4, the detection mechanism 19 is operated to determine whether the fluid drawn into the chamber 12 fulfils a predetermined compression property requirement.

If at step S4 the detection mechanism 19 determines that the contents of the chamber 12 fulfils said predetermined compression property requirement, the process proceeds to step S5. At step S5, the receptacle 3 and piston 4 are moved relative to the housing 2 such that the receptacle 3 is moved to the first dispensing position. At step S6, the piston 4 is moved relative to the receptacle 3 to expel medicament M from the chamber 12 via the first outlet 8. The process then returns to step S1 and may be repeated.

If at step S4 the detection mechanism 19 determines that the contents of the chamber 12 does not fulfil said predetermined compression property requirement, the process proceeds to step S7. At step S7, the receptacle 3 and piston 4 are moved relative to the housing 2 such that the receptacle 3 is moved to the second dispensing position. At step S8, the piston 4 is moved relative to the receptacle 3 to expel medicament M from the chamber 12 via the second outlet 9. The process then returns to step S1 and may be repeated.

One or more of steps S1 to S8 may be performed by the controller 15. In one embodiment, all of steps S1 to S8 are performed by the controller 15. In some embodiments, the controller 15 comprises a memory and a processor. The memory stores instructions that are carried out by the processor to perform one or more of steps S1 to S8. Alternatively, or additionally, one or more of steps S1 to S8 may be triggered manually by the user. For instance, once the receptacle 3 has moved to the first dispensing position, the user may actuate the input device, for example, a switch or button, to send a signal to the actuator unit to dispense the medicament M from the chamber 12.

In some embodiments, the medical pump 1 performs a priming operation. The priming operation is performed to remove air from the medical pump 1. The priming operation may be performed when the medical pump 1 is first operated, for example, in the embodiment described above in relation to FIG. 8, the priming operation may be performed prior to step S1 and may be performed by the controller 15.

The priming operation involves: locating the receptacle 3 in the filling position; moving the piston 4 relative to the receptacle 3 to draw medicament M into the chamber 12 from the inlet 7; moving the receptacle 3 and piston 4 relative to the housing 2 such that the receptacle 3 is moved to the second dispensing position; and, moving the piston 4 relative to the receptacle 3 to expel medicament M and/or air from the chamber 12 via the second outlet 9. Optionally, these steps may be repeated a predetermined number of times and then steps S1 to S8 are performed to deliver medicament to the patient.

When the medicament source 18 is first connected to the inlet 7, air may be present in the medical pump 1, for example, air may be present in the chamber 12 and/or in the inlet 7. The priming operation helps to purge the medical pump 1 of air such that medicament M is present in the chamber 12 and inlet 7.

In an alternative embodiment, the priming operation comprises: locating the receptacle 3 in the filling position; moving the piston 4 relative to the receptacle 3 to draw medicament M into the chamber 12 from the inlet 7; moving the receptacle 3 and piston 4 relative to the housing 2 such that the receptacle 3 is moved to the first dispensing position; and, moving the piston 4 relative to the receptacle 3 to expel medicament M and/or air from the chamber 12 via the first outlet 8. This helps to reduce the presence of air in the first outlet 8 and medicament delivery member. In such an embodiment, the priming operation is performed before the medicament delivery member is fluidly connected to the patient. This prevents air expelled from the medicament delivery member during the priming operation from being delivered to the patient's body. Once the priming operation has been completed, the medicament delivery member is then arranged to deliver medicament to the patient's body. For instance, if the medicament delivery member comprises a needle, then the needle is inserted into the patient's skin after the priming operation has been completed.

In some embodiments, the medical pump 1 is configured to perform an occlusion detection operation. The medical pump 1 may comprise an occlusion detection mechanism (not shown) configured to determine whether the patient's body exceeds a predetermined occlusion property, which may be the presence of a vascular occlusion. In the present embodiment, the occlusion detection mechanism comprises the controller 15, the first and/or second actuator 16, 17 of the actuator unit, and an occlusion sensor (not shown). The occlusion sensor is configured to detect information indicative of whether the drug delivery site of the patient's body exceeds a predetermined occlusion property. In an alternative embodiment, the controller 15 and first and second actuators 16, 17 do not form part of the occlusion detection mechanism and instead the detection mechanism comprises a further controller (not shown).

With the receptacle 3 in the first dispensing position, the occlusion detection mechanism is operated to determine whether the drug delivery site of the patient's body exceeds a predetermined occlusion property. In more detail, the second actuator 17 is operated to urge the piston 4 in the second direction Y relative to the receptacle 3 and the receptacle 3 is held axially stationary relative to the housing 2. This causes the medicament M received in the space 12A to be delivered to the drug delivery site of the patient's body. The occlusion sensor (not shown) detects whether an occlusion is present during the delivery of the medicament M to the patient's body. The presence of an occlusion, for example, a blockage of a blood vessel in the patient's body at the drug delivery site, will reduce the flow rate at which the medicament M is delivered to the drug delivery site. In one embodiment, the occlusion sensor detects the flow rate of the medicament M being delivered to the patient's body. If the flow rate exceeds a predetermined amount, then the occlusion detection mechanism determines that no occlusion is present. However, if the flow rate is equal or less than said predetermined amount, then the occlusion detection mechanism determines that an occlusion is present. Alternatively, or additionally, the occlusion is determined based on a change in the flow rate detected by the occlusion sensor. For example, if during the delivery of medicament M to the drug delivery site the flow rate suddenly reduces by more than a predetermined amount then the occlusion detection mechanism determines that an occlusion is present.

In yet another embodiment, the occlusion detection mechanism is configured to detect the force applied by the first and/or second actuator 16, 17 to deliver a predetermined amount of medicament to the drug delivery site of the patient. For example, the occlusion detection mechanism may comprise an occlusion sensor that determines the force required to move the piston 4 relative to the receptacle 3 by a predetermined distance to deliver a predetermined volume of medicament M to the patient. The presence of an occlusion will require a larger force to deliver medicament to the drug delivery site. If the force determined by the occlusion sensor exceeds a predetermined amount, then the occlusion detection mechanism determines that an occlusion is present. However, if the force is equal or less than a predetermined amount, then the occlusion detection mechanism determines that no occlusion is present.

In yet another embodiment, the occlusion detection mechanism is configured to detect the relative movement of the piston 4 and receptacle 3 when a predetermined force is applied by the first and/or second actuator 16, 17 to deliver medicament to the drug delivery site of the patient. For example, the occlusion detection mechanism may comprise an occlusion sensor that determines the relative displacement of the piston 4 and receptacle 3. The presence of an occlusion will result in the predetermined force causing a smaller movement of the receptacle 3 relative to the piston 4 such that a smaller volume of medicament M is delivered to the drug delivery site. If the distance of movement between the piston 4 and receptacle 3 measured by the occlusion sensor exceeds a predetermined amount, then the occlusion detection mechanism determines that no occlusion is present. However, if the distance is equal or less than a predetermined amount, then the occlusion detection mechanism determines that an occlusion is present.

In some embodiments, the sensor 20 configured to detect information indicative of whether the contents of the chamber 12 fulfils a predetermined compression requirement is the same component as the occlusion sensor.

Figure 9:
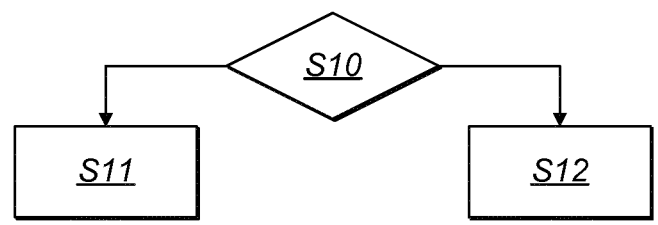
FIG. 9 is a flow diagram illustrating an occlusion detection operation of the medical pump.
Figure 10:
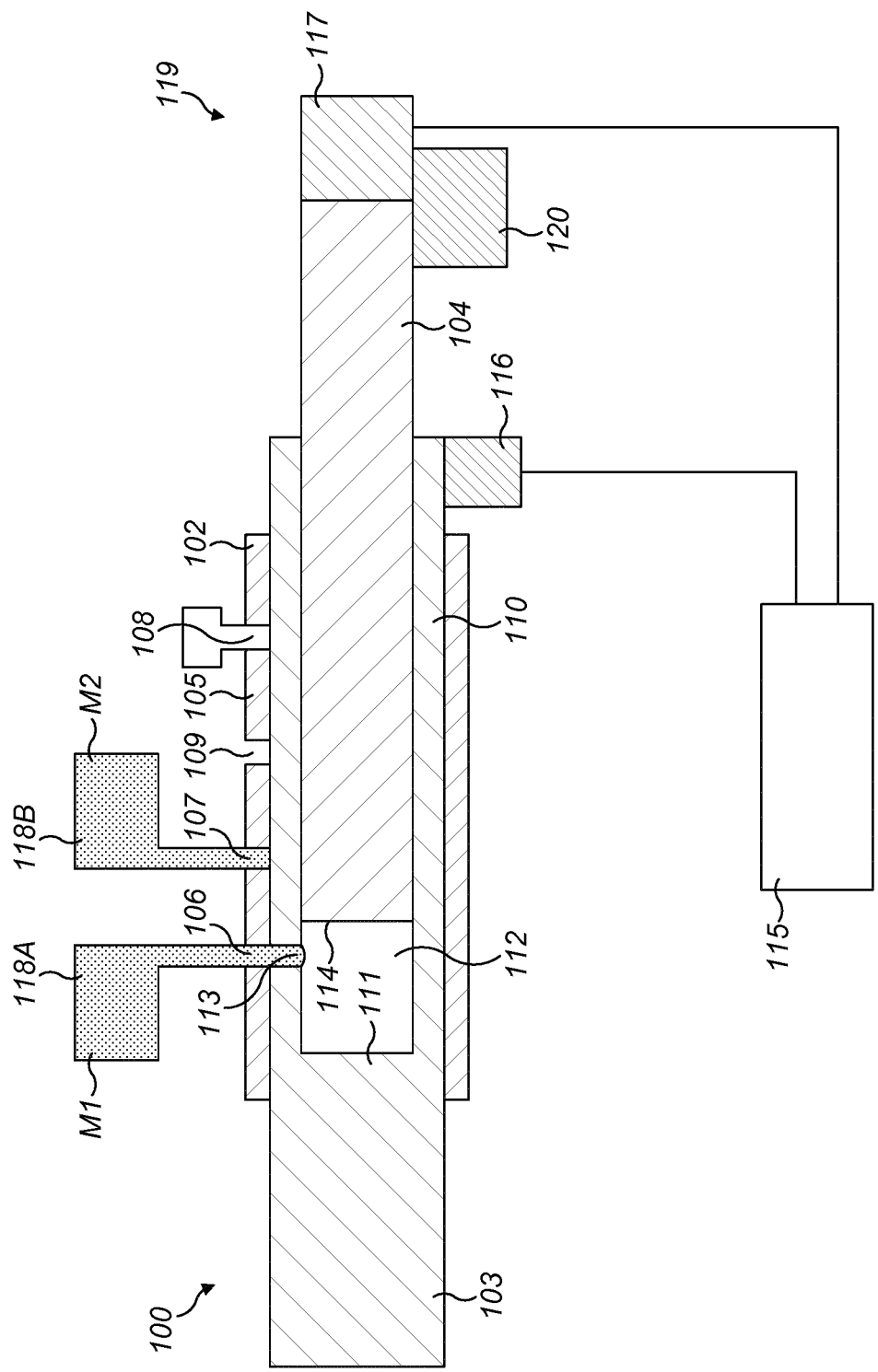
FIG. 10 is schematic cross-sectional view of a medical pump according to a second embodiment of the disclosure.

A flow diagram illustrating an example occlusion detection operation of the medical pump 1 is shown in FIG. 9. In some embodiments, one or more of the steps S10 to S12 are carried out by the controller 15.

At step S10, the receptacle 3 is located in the first dispensing position, and the occlusion detection mechanism (not shown) is operated to determine whether the drug delivery site of the patient's body exceeds a predetermined occlusion property. More specifically, the piston 4 is moved relative to the receptacle 3 to expel medicament M from the chamber 12 via the first outlet 8, and the occlusion sensor detects whether the drug delivery site of the patient's body exceeds a predetermined occlusion property, as described above, to determine whether an occlusion is present.

If at step S10 the occlusion detection mechanism determines that the drug delivery site of the patient's body is below a predetermined occlusion property, then the process proceeds to step S11. At step S11, the receptacle 3 and piston 4 are further moved relative to each other to deliver further medicament M from the chamber 12 via the first outlet 8 such that medicament M is supplied to the patient. The process then returns to step S10 and may be repeated.

If at step S10 the occlusion detection mechanism determines that the drug delivery site of the patient's body is equal to or greater than a predetermined occlusion property, and thus an occlusion is present, then the process proceeds to step S12. At step S12, an alarm is activated to alert the patient to the presence of the occlusion. In some embodiments, the alarm comprises a visual alarm, such as a light, and/or an audible alarm, such as a speaker. Additionally, or alternatively, the occlusion detection mechanism may halt the drug delivery process such that no further medicament M is delivered to the drug delivery site.

One or more of steps S10 to S12 may be performed by the controller 15. In one embodiment, all of steps S10 to S12 are performed by the controller 15. In some embodiments, the controller 15 comprises a memory and a processor, whereby the memory stores instructions that are carried out by the processor to perform one or more of steps S10 to S12. Alternatively, or additionally, one or more of steps S10 to S12 may be triggered manually by the user.

In some embodiments, steps S10 to S12 are performed after steps S1 to S8. Alternatively, the occlusion detection operation of steps S10 to S12 may be performed instead of step S6 in the process illustrated in FIG. 8. The process then returns to step S1 and may be repeated. In yet another embodiment, the occlusion detection operation is performed, for example, automatically after a predetermined period of time has elapsed, and may be repeated whenever the time period has elapsed.

In some embodiments, the medical pump 1 comprises first, second and third seals 21, 22, 23. The first seal 21 is configured to provide a seal between the housing 2 and receptacle 3 about the inlet 7. The first seal 21 prevents the leakage of medicament M between the housing 2 and receptacle 3 when fluid is drawn into the chamber 12 from the inlet 7. In one embodiment, the first seal 21 comprises first and second O-rings 21A, 21B that are axially spaced on opposite sides of the inlet 7. The first and second O-rings 21A, 21B provide a seal about the inlet 7 whilst allowing for movement of the receptacle 3 relative to the housing 2. The first and second O-rings 21A, 21B may be mounted to the housing 2 or receptacle 3.

The second seal 22 is configured to provide a seal between the housing 2 and receptacle 3 about the first outlet 8. The second seal 22 prevents the leakage of medicament M between the housing 2 and receptacle 3 when fluid in the chamber 12 is expelled from the first outlet 8. In one embodiment, the second seal 22 comprises first and second O-rings 22A, 22B that are axially spaced on opposite sides of the first outlet 8. The first and second O-rings 22A, 22B provide a seal about the first outlet 8 whilst allowing for movement of the receptacle 3 relative to the housing 2. The first and second O-rings 22A, 22B may be mounted to the housing 2 or receptacle 3.

The third seal 23 is configured to provide a seal between the housing 2 and receptacle 3 about the second outlet 9. The third seal 23 prevents the leakage of medicament M between the housing 2 and receptacle 3 when fluid in the chamber 12 is expelled from the second outlet 9. In one embodiment, the third seal 23 comprises the first O-ring 22A of the second seal 22 and an additional O-ring 23A. The first O-ring 22A of the second seal 22 and the additional O-ring 23A are axially spaced on opposite sides of the second outlet 9 to provide a seal about the second outlet 9 whilst allowing for movement of the receptacle 3 relative to the housing 2. The additional O-ring 23A may be mounted to the housing 2 or receptacle 3.

In one embodiment, the first, second and third seals 21, 22, 23 are adhered to the housing 2 or receptacle 3. However, in another embodiment the first, second and third seals 21, 22, 23 may be formed with the housing 2 or receptacle 3. For example, the first, second and third seals 21, 22, 23 and the housing 2 or receptacle 3 could be injection molded, for instance, using a multi-material injection molding technique such as multi-component injection molding, multi-shot injection molding or over-molding.

The piston 4 being received in the receptacle 3 and the receptacle 3 being received in the housing 2 makes the medical pump 1 more compact in the direction of the central axis A-A. The receptacle 3 only needs to be axially moveable relative to the housing 2 sufficient distance to allow for the passage 13 to be fluidly communicated with each of the inlet 7, first outlet 8 and second outlet 9. Furthermore, the piston 4 only needs to be axially moveable relative to the receptacle 3 sufficient distance to draw medicament M into the chamber 12 and expel medicament M from the chamber 12.

In some embodiments, the piston 4 comprises a seal 24 that is configured to provide a seal between the piston 4 and the internal surface of the peripheral wall 10 of the receptacle 3. In one embodiment, the seal 24 of the piston 4 comprises first and second O-rings 24A, 24B that are axially spaced and are located proximate to the end 14 of the piston 4. In another embodiment (not shown), the piston 4 comprises a stopper, for example, a rubber stopper, at the end 14 of the piston 4, wherein the stopper seals against the internal surface of the peripheral wall 10 of the receptacle 3.

In an alternative embodiment (not shown), the inlet 7 is fluidly connected to a source of bodily fluid, for example, a source of blood. The source of bodily fluid may be a container of bodily fluid. Alternatively, the source of bodily fluid may be the user's body, which is connected to the inlet 7 via a needle and/or tube. Thus, the medical pump 1 is configured to draw bodily fluid into the chamber 12. In one embodiment, the first outlet 8 is connected to a container for collecting bodily fluid. Thus, the medical pump 1 is configured to draw bodily fluid into the chamber 12 and then dispense the bodily fluid to the container for storage. Alternatively, or additionally, the first outlet 8 is fluidly connected to a sensor unit (not shown) configured to detect information indicative of a property of the bodily fluid expelled from the first outlet 8.

In one alternative embodiment (not shown), the second outlet 9 is omitted such that the housing comprises one inlet 7 and one outlet 8.

In one alternative embodiment (not shown), the detection mechanism 19 is omitted.

Referring now to FIGS. 10 to 16, a medical pump 100 according to a second embodiment is shown. As with the first embodiment, the medical pump 100 of the second embodiment comprises a housing 102, a receptacle 103 and a piston 104, wherein the housing 102 comprises a peripheral wall 105 that slidably receives the receptacle 103. The housing 102 comprises first and second inlets 106, 107 and first and second outlets 108, 109. The first and second inlets 106, 107 and first and second outlets 108, 109 may be axially spaced.

The receptacle 103 is slidably received in the housing 102. The receptacle 103 comprises a peripheral wall 110 and an end wall 111 that together define a chamber 112. The receptacle 103 comprises a passage 113 that is fluidly communicated with the chamber 112. The housing 102, receptacle 103 and piston 104 may be of a similar shape and/or arrangement to those described above in relation to the first embodiment of the medical pump 1, except that the housing 102 of the second embodiment comprises first and second inlets 106, 107 instead of a single inlet 7.

The receptacle 103 is axially moveable relative to the housing 102 to selectively fluidly communicate the passage 113 with the first and second inlets 106, 107 and first and second outlets 108, 109, as is described in more detail below.

The receptacle 103 has an open end that is remote to the end wall 111 and is configured to receive the piston 104 such that an end 114 of the piston 104 is received in the chamber 112. The piston 104 is axially moveable relative to the receptacle 103. More specifically, the piston 104 is moveable relative to the receptacle 103 in a first direction (shown by arrow 'X' in FIGS. 12 and 13), wherein the piston 104 is moved axially away from the end wall 111 of the receptacle 103, and a second direction (shown by arrow 'Y' in FIGS. 15 and 16), wherein the piston 104 is moved axially towards the end wall 111 of the receptacle 103.

The medical pump 100 further comprises an actuator unit and a controller 115. The actuator unit is similar to the actuator unit of the first embodiment and therefore a detailed description is not repeated herein. Briefly, the actuator unit comprises a first actuator 116 that is operable to axially move the receptacle 103 and a second actuator 117 that is operable to axially move the piston 104. As with the first embodiment, the medical pump 100 of the second embodiment is configured such that the receptacle 103 may be locked in position relative to the housing 102 to prevent axial movement of the receptacle 103 relative to the housing 102. Alternatively, or additionally, the medical pump 100 is configured such that the piston 104 may be locked in position relative to the housing 102 to prevent axial movement of the piston 104 relative to the housing 102.

A first medicament source 118A is fluidly connected to the first inlet 106 of the housing 102. The first medicament source 118A comprises a reservoir containing a first medicament M1. A second medicament source 118B is fluidly connected to the second inlet 107 of the housing 102. The second medicament source 118B comprises a reservoir containing a second medicament M2.

The first outlet 108 is fluidly connected to a medicament delivery member (not shown), for example, a needle or flexible tubing, that is configured to deliver medicament from the first outlet 108 to the user's body. The second outlet 109 is fluidly connected to a container (not shown) for receiving fluid expelled from the second outlet 109.

The medical pump 100 further comprises a detection mechanism 119 that is configured to determine whether the contents of the chamber 112 fulfils a predetermined compression requirement. In the present embodiment, the detection mechanism is connected to a sensor 120 to detect information indicative of whether the contents of the chamber 112 fulfils a predetermined compression requirement. The detection mechanism 119 is similar to the detection mechanism 19 of the medical pump 1 of the first embodiment and therefore a description thereof will not be repeated herein.

Figure 11:
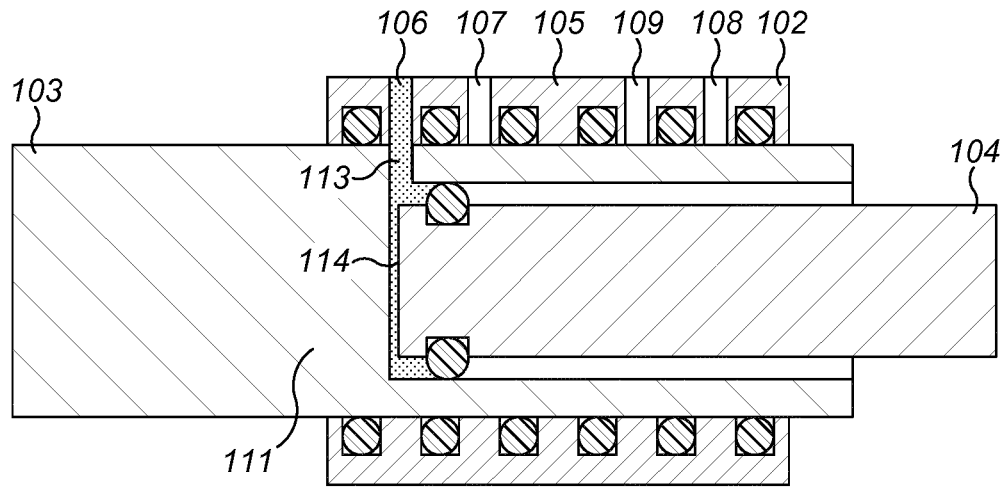
FIG. 11 is a schematic cross-sectional view of part of a housing, receptacle and piston of the medical pump of FIG. 10, wherein the receptacle is in a first filling position.

An exemplary operation of the medical pump 100 will now be described with reference to FIGS. 11 to 16. The receptacle 103 is initially in a first filling position and the end 114 of the piston 104 abuts the end wall 111 of the receptacle 103 (as shown in FIG. 11), wherein the passage 113 of the receptacle 103 is aligned with the first inlet 106 of the housing 102 and therefore the first medicament source 118A is fluidly communicated with the chamber 112 via the first inlet 106 and passage 113.

Figure 12:
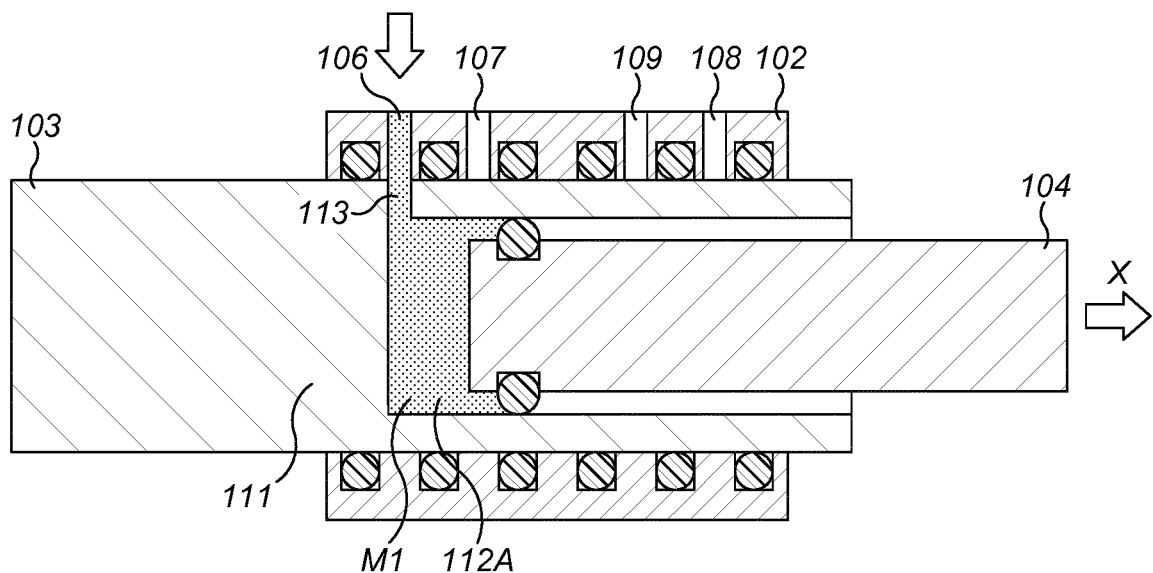
FIG. 12 is a schematic cross-sectional view of the housing, receptacle and piston of FIG. 11, wherein the receptacle is in the filling position and liquid is drawn into the receptacle.

With the receptacle 103 in the first filling position, the second actuator 117 is then operated to move the piston 104 axially in the first direction X relative to the housing 102 and receptacle 103. This causes the end 114 of the piston 104 to move away from the end wall 111 of the receptacle 103 such that a space 112A is formed therebetween (as shown in FIG. 12). The movement of the piston 104 in the first direction X creates a suction effect that causes the first medicament M1 from the first medicament source 118A to be drawn into the chamber 112, via the first inlet 106 and passage 113, to fill the space 112A.

Figure 13:
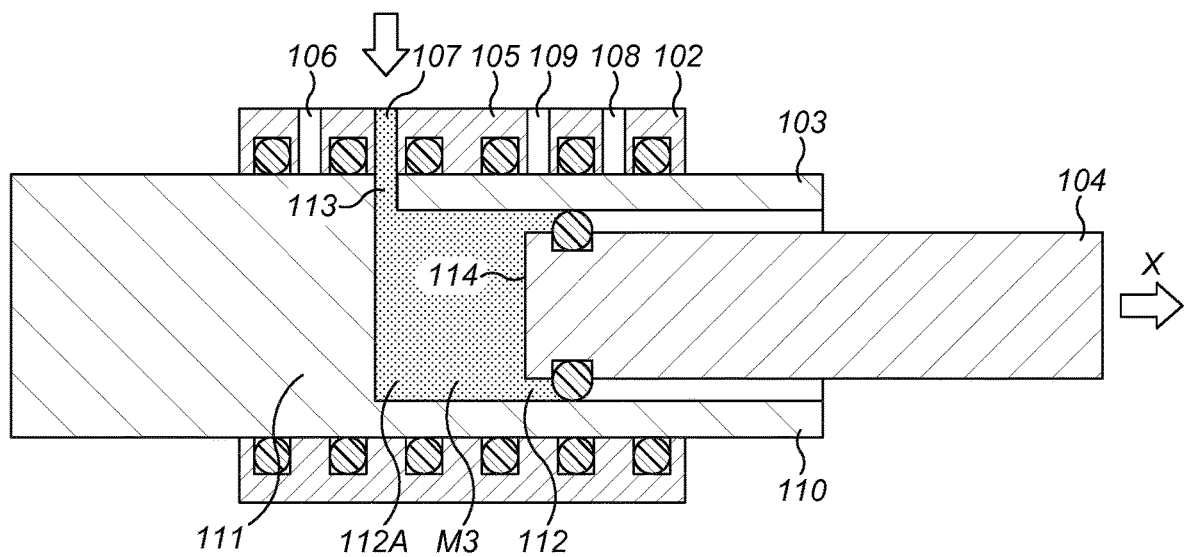
FIG. 13 is a schematic cross-sectional view of the housing, receptacle and piston of FIG. 11, wherein the receptacle is in a second filling position.

The receptacle 103 is then moved to a second filling position (as shown in FIG. 13), wherein the passage 113 of the receptacle 103 is aligned with the second inlet 107 of the housing 102 and therefore the second medicament source 118B is fluidly communicated with the chamber 112 via the second inlet 107 and passage 113. To move the receptacle 103 to the second filling position, the first actuator 116 is operated to move the receptacle 103 axially in the first direction X relative to the housing 102. In one embodiment, the second actuator 117 is simultaneously operated to move the piston 104 a corresponding distance in the first direction X.

With the receptacle 103 in the second filling position, the second actuator 117 is operated to move the piston 104 axially in the first direction X relative to the housing 102 and receptacle 103. This causes the end 114 of the piston 104 to move further away from the end wall 111 of the receptacle 103 such that the size of the space 112A is increased. The movement of the piston 104 in the first direction X creates a suction effect that causes the second medicament M2 from the second medicament source 118B to be drawn into the chamber 112, via the second inlet 107 and passage 113, to fill the space 112A. Therefore, the chamber 112 contains a mixture M3 of the first and second medicaments M1, M2.

In some embodiments (not shown), the first medicament source 118A contains a first medicament M1 and the second medicament source 118B contains a carrier that is mixed with the first medicament M1 in the chamber 112. The first medicament M1 in the first medicament source 118A may be stored in solid form and the carrier may comprise a liquid that is mixed with the first medicament M1 to allow the first medicament M1 to be delivered to the drug delivery site as part of a liquid mixture M3. This is particularly advantageous if the first medicament M1 should be stored in solid form, for example, if the first medicament M1 is more stable in solid form than in liquid form.

Figure 14:
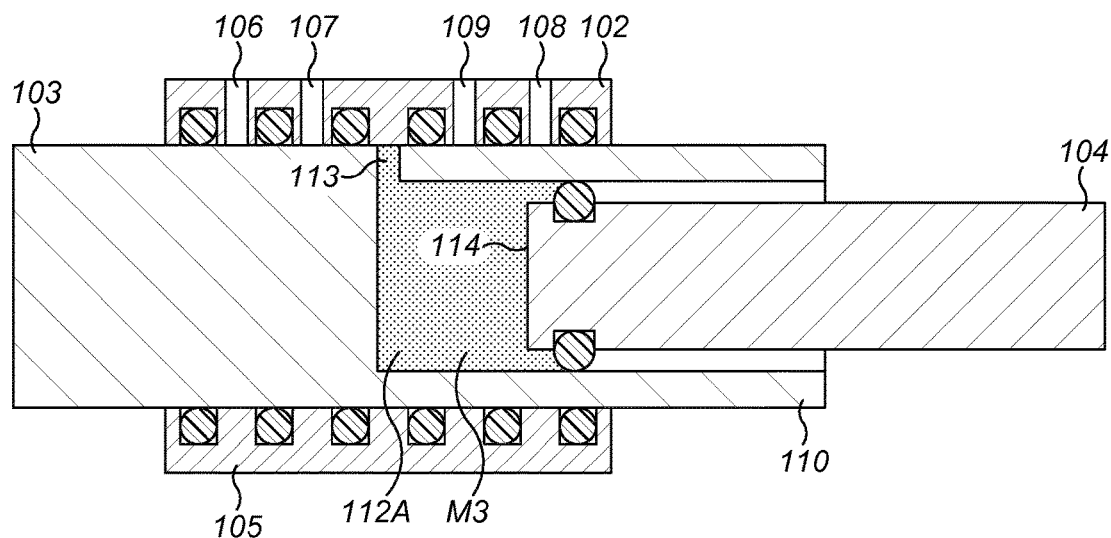
FIG. 14 is a schematic cross-sectional view of a housing, receptacle and piston of FIG. 11, wherein the receptacle is in a detection position.

The receptacle 103 is then moved to a detection position (as shown in FIG. 14), wherein the passage 13 of the receptacle 103 is not aligned with any of the first inlet 106, second inlet 107, first outlet 108 and second outlet 109. Thus, the mixture M3 contained in the chamber 112 is not fluidly communicated with any of the first inlet 106, second inlet 107, first outlet 108 and second outlet 109 and instead the space 112A is sealed.

To move the receptacle 103 to the detection position, the first actuator 116 is operated to move the receptacle 103 axially in the first direction X relative to the housing 102. The piston 104 also moves by the same distance in the first direction X such that the relative position of the receptacle 103 with respect to the piston 104 is unchanged. In one embodiment, the second actuator 117 is simultaneously operated to move the piston 104 together with the receptacle 103 to the detection position.

With the receptacle 103 in the detection position, the detection mechanism 119 is operated to determine whether the contents of the space 112A in the chamber 112 fulfils a predetermined compression property requirement. As with the first embodiment, the detection of whether the contents fulfils the predetermined compression property requirement allows for the detection mechanism 119 to assess whether gas or gas bubbles are present in the space 112A in the chamber 112 along with the mixture M3.

The detection mechanism 119 operates in a similar manner to the detection mechanism 19 of the first embodiment. For example, the second actuator 117 may operated to urge the piston 104 in the second direction Y relative to the receptacle 103. The relative movement of the receptacle 103 and piston 104 when the receptacle 103 is in the detection position compresses the contents of the space 112A. The predetermined compression property requirement is fulfilled if the contents of the space 112A is compressed by less than a predetermined amount. As discussed above, this predetermined amount may relate to the distance that the piston 104 is moved relative to the receptacle 103 when the receptacle 103 is in the detection position and the corresponding actuator 116, 117 is operated. Alternatively, the predetermined amount of compression may relate to a defined volume of the space 112A to which the contents of the space 112A may just be compressed when no hazardous amount of gas is present in the space 112A. Alternatively, the predetermined amount of compression may relate or be determined via the force necessary to move one of the receptacle 103 and piston 104 a given axial distance towards the other one of the receptacle 103 and piston 104.

If a critical or hazardous amount of gas is present in the space 112A, the contents of the space 112A is compressed by more than the predetermined amount upon relative movement of the receptacle 103 and piston 104. This is due to a greater compressibility of the contents of the space 112A because gas has a compressibility which is greater than that of liquid.

Said distance, volume or force may be monitored by the controller 115 or an additional element or gauge of the medical pump 100 during the operation of the detection mechanism 119. To this effect, the controller 115 may compare the respective variable chosen from distance, volume or force, as mentioned above, to a threshold value which is stored by the controller 115 and separates acceptable values of the respective variable from non-acceptable values.

Figure 15:
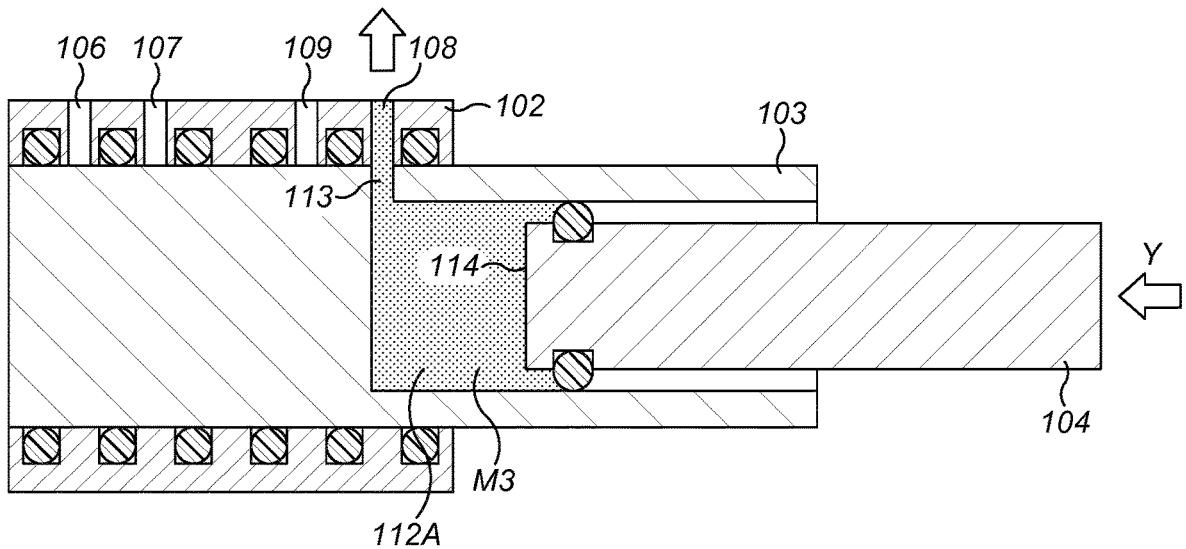
FIG. 15 is a schematic cross-sectional view of a housing, receptacle and piston of FIG. 11, wherein the receptacle is in a first dispensing position; and, FIG. 16 is a schematic cross-sectional view of a housing, receptacle and piston of FIG. 11, wherein the receptacle is in a second dispensing position.

If the detection mechanism 119 determines that the chamber 112 is sufficiently free of gas that the predetermined compression property requirement is fulfilled, then the receptacle 103 is moved relative to the housing 102 to a first dispensing position wherein the passage 113 of the receptacle 103 is aligned with the first outlet 108 (see FIG. 15). Thus, the mixture M3 in the chamber 112 is fluidly communicated with the first outlet 108 via the passage 113.

To move the receptacle 103 to the first dispensing position, the first actuator 116 is operated to move the receptacle 103 axially in the first direction X relative to the housing 102. The piston 104 also moves by the same distance in the first direction X such that the relative position of the receptacle 103 with respect to the piston 104 is unchanged. With the receptacle 103 in the first dispensing position, the second actuator 117 is operated to move the piston 104 axially in the second direction Y relative to the housing 102 and receptacle 103. This causes the end 114 of the piston 104 to move towards the end wall 111 of the receptacle 103 such that size of the space 112A reduces and thus the mixture M3 in the chamber 112 is expelled out of the passage 113 in the receptacle 103 and dispensed through the first outlet 108. Thus, the mixture M3 is delivered to the user's body via the medicament delivery member (not shown).

Once the mixture M3 has been expelled from the chamber 112, the receptacle 103 is moved from the first dispensing position to the first filling position (shown in FIG. 11) and the above process may be repeated.

Figure 16:
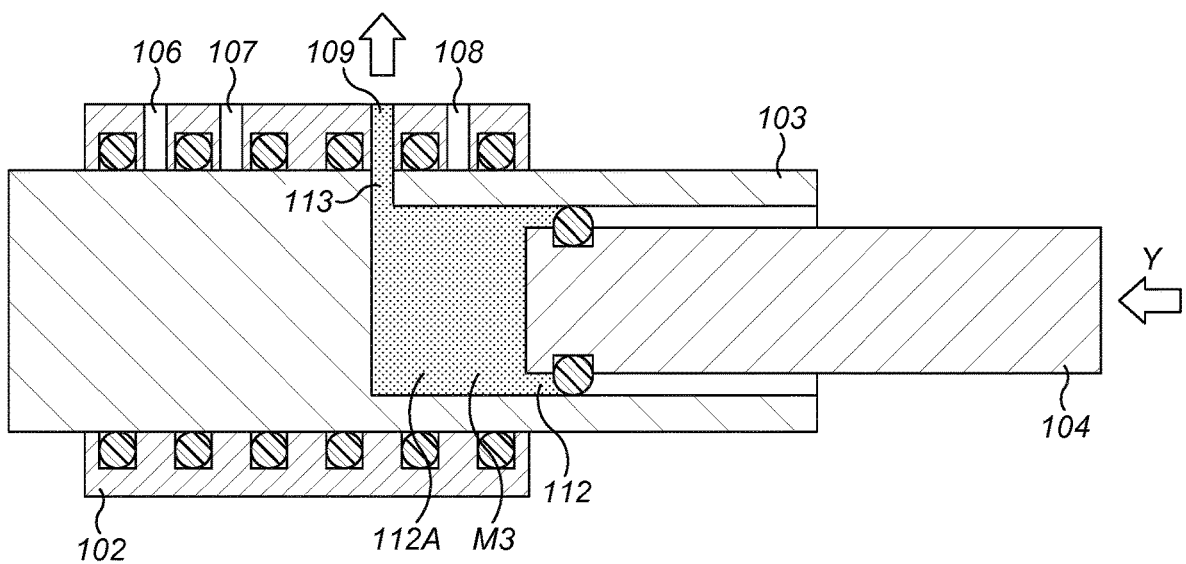

If the detection mechanism 119 determines that the chamber 112 contains sufficient gas that the predetermined compression property requirement is not fulfilled, then the receptacle 103 is moved relative to the housing 102 to a second dispensing position wherein the passage 113 of the receptacle 103 is aligned with the second outlet 109 (see FIG. 16). Thus, the mixture M3 in the chamber 112 is fluidly communicated with the second outlet 109 via the passage 113.

To move the receptacle 103 to the second dispensing position, the first actuator 116 is operated to move the receptacle 103 axially in the first direction X relative to the housing 102. The piston 104 also moves by the same distance in the first direction X such that the relative position of the receptacle 103 with respect to the piston 104 is unchanged. With the receptacle 103 in the second dispensing position, the second actuator 117 is operated to move the piston 104 axially in the second direction Y relative to the housing 102 and receptacle 103. This causes the end 114 of the piston 104 to move towards the end wall 111 of the receptacle 103 such that size of the space 112A reduces and thus the mixture M3 in the chamber 112 is expelled out of the passage 113 in the receptacle 103 and dispensed through the second outlet 109. Thus, the mixture M3 is delivered to the container (not shown) that is fluidly connected to the second outlet 109. The medicament M3 in the container may then be disposed of.

Once the mixture M3 has been expelled from the chamber 112, the receptacle 103 is moved from the second dispensing position to the first filling position (shown in FIG. 11) and the above process may be repeated.

The piston 104 being received in the receptacle 103 and the receptacle 103 being received in the housing 102 makes the medical pump 100 more compact in the direction of the central axis A-A. The receptacle 103 only needs to be axially moveable relative to the housing 102 sufficient distance to allow for the passage 113 to be fluidly communicated with each of the first and second inlets 106, 107 and first and second outlets 108, 109. Furthermore, the piston 104 only needs to be axially moveable relative to the receptacle 103 sufficient distance to draw the first and second medicaments M1, M2 into the chamber 112 and expel the mixture M3 from the chamber 112.

In one embodiment, the medical pump 100 further comprises a sensor unit configured to detect information indicative of a property of the bodily fluid expelled from the first outlet 108.

In one embodiment, the first inlet 106 is connected to a source of bodily fluid, for example, a container of bodily fluid or directly to the user's body via a needle and/or tube. Thus, the medical pump 100 is configured to draw bodily fluid into the chamber 112. The second inlet 107 is connected to a liquid source comprising a further liquid, for example, a reactant or reagent. Thus, the medical pump 100 is configured to draw the further into the chamber 112 to mix with the bodily fluid in the chamber 112. The medical pump 100 may further comprise a sensor unit (not shown) configured to detect information indicative of a property of the bodily fluid expelled from the first outlet 108. The further liquid may react with the bodily fluid, either in the chamber 112 or when dispensed to the sensor unit. The bodily fluid and further liquid may be analysed by the sensor unit. The further liquid may be a reagent or reactant and/or comprise a medical substance which may be suitable to react with the bodily fluid in order to allow for a blood glucose measurement. The sensor unit may be suitable to perform such a blood glucose measurement.

In one embodiment, the second inlet 107 and detection mechanism 119 is omitted.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

In some embodiments, the medical pump 1, 100 is configured to move the receptacle 3 relative to the housing 2 to a storage position when the medical pump 1, 100 is in an idle state, for example, when the medical pump 1, 100 not operated to deliver medicament to the patient. In the storage position, the passage 13, 113 is not fluidly communicated with any of the inlet 7, first inlet 106 or second inlet 107. Thus, if pressure is applied to the medicament source 18 or first and second medicament sources 118A, 118B to urge fluid from the medicament sources 18, 118A, 118B, then the fluid will not enter the chamber 12, 112. This is particularly advantageous if the medicament source 18 or first and second medicament sources 118A, 118B comprise a flexible bag, which otherwise may easily be squeezed by the patient to force fluid into the chamber 12, 112. In one embodiment, when the medical pump 1 is in the storage position, the passage 13, 113 is also not fluidly communicated with any of the first outlet 8, 108 and second outlet 9, 109. This helps to prevent the transfer of fluid from the first outlet 8, 108 or second outlet 9, 109 to the chamber 12, 112.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers)

and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regionsthemselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. A medical pump for dispensing a liquid, the medical pump comprising:
   a housing comprising an inlet for receiving the liquid and a first outlet for dispensing the liquid;
   a receptacle comprising a chamber and a passage that is in fluid communication with the chamber, wherein the receptacle is received in the housing and is axially movable relative to the housing from a filling position in which the passage fluidly communicates the chamber with the inlet to a first dispensing position in which the passage fluidly communicates the chamber with the first outlet; and
   a piston that is received in the chamber and is configured such that, when the receptacle is in the filling position, the piston is axially moveable relative to the receptacle to draw the liquid from the inlet into the chamber, and when the receptacle is in the first dispensing position, the piston is axially moveable relative to the receptacle to dispense the liquid in the chamber through the first outlet,
   wherein the piston and an end wall of the receptacle are configured to be spaced apart by a substantially constant distance as the receptacle moves to the filling position and as the receptacle moves to the first dispensing position,
   wherein the housing further comprises a second outlet, wherein the receptacle is axially movable relative to the housing to a second dispensing position in which the passage fluidly communicates the chamber with the second outlet,
   wherein the piston is configured such that when the receptacle is in the second dispensing position, the piston is axially moveable relative to the receptacle to dispense the liquid contained in the chamber through the second outlet, and
   wherein the medical pump further comprises a detection mechanism configured to:
      determine whether contents of the chamber fulfil a predetermined compression property requirement,
      move the receptacle to the second dispensing position, and then
      move the receptacle and the piston relative to each other to dispense the liquid in the chamber through the second outlet if the predetermined compression property requirement is not fulfilled.

2. A medical pump according to claim 1, wherein the receptacle is lockable relative to the housing to prevent axial movement of the receptacle relative to the housing.

3. A medical pump according to claim 1, wherein the receptacle and the piston are configured to move together relative to the housing at substantially the same speed as the receptacle moves to the filling position and as the receptacle moves to the first dispensing position.

4. A medical pump according to claim 1, wherein the receptacle comprises a peripheral wall that extends about the chamber.

5. A medical pump according to claim 4, wherein the passage extends through the peripheral wall of the receptacle.

6. A medical pump according to claim 1, wherein the housing comprises a peripheral wall that extends about the receptacle received in the housing.

7. A medical pump according to claim 6, wherein the inlet and the first outlet each comprises a respective aperture in the peripheral wall of the housing.

8. A medical pump according to claim 1, wherein the housing further comprises an opening, wherein the receptacle is axially movable relative to the housing to a third position in which the passage fluidly communicates the chamber with the opening.

9. A medical pump according to claim 8, wherein the piston is configured such that when the receptacle is in the third position, the piston is axially moveable relative to the receptacle to induce a flow of the liquid between the chamber and the opening.

10. A medical pump according to claim 1, wherein the housing further comprises a second inlet for receiving a second liquid, wherein the receptacle is axially movable relative to the housing to a second filling position in which the passage fluidly communicates the chamber with the second inlet.

11. A medical pump according to claim 10, wherein the piston is configured such that when the receptacle is in the second filling position, the piston is axially moveable relative to the receptacle to draw the second liquid into the chamber from the second inlet.

12. A medical pump according to claim 1, wherein the detection mechanism is configured to move the receptacle to a detection position in which the chamber is not fluidly communicated with any of the inlet, the first outlet, and the second outlet.

13. A medical pump according to claim 12, wherein the detection mechanism is configured to move the receptacle and the piston relative to each other when the receptacle is in the detection position to detect information indicative of whether the contents of the chamber fulfil the predetermined compression property requirement.

14. A medical pump according to claim 1, further comprising a sensor unit configured to detect information indicative of a property of the liquid expelled from the chamber.

15. A medical pump according to claim 1, further comprising a medicament source to which the inlet is connected.

16. A medical pump according to claim 15, wherein the medicament source comprises a medicament.

17. A method of operating a medical pump, the medical pump comprising a housing having an inlet and a first outlet, a receptacle having a chamber and a passage that is in fluid communication with the chamber, and a piston that is received in the chamber, the method comprising:
    providing the receptacle in a filling position within the housing in which the passage fluidly communicates the chamber with the inlet;
    moving the piston axially relative to the receptacle to draw liquid into the chamber from the inlet while the receptacle is in the filling position;
    moving the receptacle axially relative to the housing to a first dispensing position in which the passage fluidly communicates the chamber with the first outlet; and
    moving the piston axially relative to the receptacle to dispense the liquid in the chamber through the first outlet while the receptacle is in the first dispensing position,
    wherein the piston and an end wall of the receptacle are spaced apart by a substantially constant distance as the receptacle moves to the filling position and as the receptacle moves to the first dispensing position,
    wherein the housing further comprises a second outlet, wherein the receptacle is axially movable relative to the housing to a second dispensing position in which the passage fluidly communicates the chamber with the second outlet,
    wherein the piston is configured such that when the receptacle is in the second dispensing position, the piston is axially moveable relative to the receptacle to dispense the liquid contained in the chamber through the second outlet, and
    wherein the medical pump further comprises a detection mechanism configured to:
        determine whether contents of the chamber fulfil a predetermined compression property requirement,
        move the receptacle to the second dispensing position, and then
        move the receptacle and the piston relative to each other to dispense the liquid in the chamber through the second outlet if the predetermined compression property requirement is not fulfilled.

* * * * *